US012412360B2

(12) United States Patent
Li et al.

(10) Patent No.: US 12,412,360 B2
(45) Date of Patent: Sep. 9, 2025

(54) DIGITAL IMAGE STITCHING SYSTEMS AND METHODS FOR GENERATING ONE OR MORE PANORAMIC IMAGE VIEWS

(71) Applicant: The Procter & Gamble Company, Cincinnati, OH (US)

(72) Inventors: Pei Li, Eschborn (DE); Faiz Feisal Sherman, Mason, OH (US); Xinru Cui, Beijing (CN); Kai-Ju Cheng, Taoyuan (TW); Kuan-Chung Chen, Taoyuan (TW); Shao-Ang Chen, Taoyuan (TW); Jia-Chyi Wang, Taoyuan (TW); Yu-Cheng Chien, Taoyuan (TW)

(73) Assignee: The Procter & Gamble Company, Cincinnati, OH (US)

( * ) Notice: Subject to any disclaimer, the term of this patent is extended or adjusted under 35 U.S.C. 154(b) by 376 days.

(21) Appl. No.: 18/124,790

(22) Filed: Mar. 22, 2023

(65) Prior Publication Data

US 2023/0306706 A1   Sep. 28, 2023

(30) Foreign Application Priority Data

Mar. 24, 2022   (WO) ................ PCT/CN2022/082673

(51) Int. Cl.
*G06K 9/00*   (2022.01)
*A61B 1/24*   (2006.01)
(Continued)

(52) U.S. Cl.
CPC ................ *G06V 10/16* (2022.01); *G06T 3/60* (2013.01); *G06T 7/0012* (2013.01); *G06T 7/20* (2013.01);
(Continued)

(58) Field of Classification Search
CPC ............ A16B 1/24; G06K 9/00; G06V 10/16
(Continued)

(56) References Cited

U.S. PATENT DOCUMENTS

2013/0286174 A1* 10/2013 Urakabe .................. A61B 1/04
                                                                348/66
2018/0184891 A1*  7/2018 Elazar .................. A61B 5/0088
(Continued)

OTHER PUBLICATIONS

Retracted: Machine Learning Techniques for Human Age and Gender Identification Based on Teeth X-Ray Images Journal of Healthcare Engineering Received Oct. 10, 2023; Accepted Oct. 10, 2023; Published Oct. 11, 2023 (Year: 2023).*
(Continued)

*Primary Examiner* — Seyed H Azarian
(74) *Attorney, Agent, or Firm* — Matthew J. Spegele

(57) ABSTRACT

Digital image stitching systems and methods are disclosed herein for generating one or more panoramic image views. A plurality of digital images depicting a target feature within an application area are captured by a camera of a scanner device. Motion data is captured, by a sensor coupled to the scanner device, as the scanner device moves relative to the target feature, where relative position data, corresponding to the plurality of digital images, is determined based on the motion data. An angle or position is generated for a first image relative to a second image of the plurality of images, and, based on image matching of the angle or the position of the second image with respect to the first image, a panoramic image view is generated depicting the target feature in a wider field of view of the application area than either the first image or the second image.

29 Claims, 13 Drawing Sheets

(51) Int. Cl.
*G06T 3/60* (2006.01)
*G06T 7/00* (2017.01)
*G06T 7/20* (2017.01)
*G06T 7/70* (2017.01)
*G06V 10/10* (2022.01)
*G06V 10/44* (2022.01)
*G06V 10/74* (2022.01)

(52) U.S. Cl.
CPC ............... *G06T 7/70* (2017.01); *G06V 10/44* (2022.01); *G06V 10/761* (2022.01); *G06T 2207/30036* (2013.01); *G06T 2207/30241* (2013.01)

(58) Field of Classification Search
USPC ....... 382/100, 103, 107, 108, 120, 128, 156, 382/162, 168, 173, 181, 193, 199, 203, 382/219, 224, 254, 284–291, 305, 312; 348/66
See application file for complete search history.

(56) References Cited

U.S. PATENT DOCUMENTS

| 2019/0258690 | A1* | 8/2019 | Elbaz | H04N 13/257 |
| 2019/0269485 | A1* | 9/2019 | Elbaz | A61B 5/1079 |
| 2020/0205943 | A1* | 7/2020 | Elbaz | A61B 1/00009 |
| 2021/0068773 | A1* | 3/2021 | Moshe | G16H 30/40 |

OTHER PUBLICATIONS

"Galaxy Camera: How Do I take a Panorama photo?", Panorama, URL: https://www.samsung.com/za/support/mobile-devices/galaxy-camera-how-do-i-take-a-panorama-photo/; Apr. 25, 2018, 3 Pages.

PCT Search Report and Written Opinion for PCT/CN2022/082673 dated Sep. 9, 2022, 19 pages.

EP Search Report and Written Opinion for 23163223.3 dated May 8, 2023, 12 pages.

Kobayashi et al., "User identification based on toothbrushing information using three-axis accelerometer", DOI:10.1145/2800835. 2800889, XP058965088, Sep. 7, 2015, pp. 129-132.

* cited by examiner

DIGITAL IMAGE STITCHING SYSTEMS AND METHODS FOR GENERATING ONE OR MORE PANORAMIC IMAGE VIEWS

FIELD

The present disclosure generally relates to digital image stitching systems and methods, and more particularly to, digital image stitching systems and methods for generating one or more panoramic image views.

BACKGROUND

Conventional digital camera technology provides users with the ability to capture digital images. In many instances, the digital images are captured in a typical manner where the images have a certain dimension or resolution, which may be expressed in a pixel count of the digital image (e.g., 2048×1536 for a 3 megapixel image, 5184×3546 for an 18 mega pixel image, etc.) in a certain area (e.g., in a 6×3 inch area, etc.). Such digital images, however, typically have a limited field of view (FOV), especially when such images are captured by conventional cameras, such as those on mobile devices. Moreover, although conventional digital camera technology offers users the ability to capture movies (e.g., multiple image frames) and take "panoramic photos" that may comprise a multitude of captured images, such movies or photos are typically captured for human consumption, that is, for later viewing by human users on mobile devices and the like. Such images lack precession or orientation data in order to determine orientation of multiple images captured overtime in space when the camera is positioned, turned, or otherwise moved differently as images are captured. This is especially so when such images are captured in a small space or area, such as with in a mouth for oral imaging applications.

A problem arises, therefore, when such conventional digital images are used for digital and machine vision applications, where orientation and location in space, become important for a machine vision application or otherwise digital application to determine or classify objects within such images.

For the foregoing reasons, there is a need for digital image stitching systems and methods for generating one or more panoramic image views to allow for enhanced imaging precision, as further described herein.

SUMMARY

As described herein, digital image stitching systems and methods are disclosed for generating one or more panoramic image views. Such digital image stitching systems and methods provide digital imaging based solutions for overcoming problems that arise from correctly identifying orientations, dimensions, and locations in space for machine vision applications or otherwise digital image applications. The digital image stitching systems and methods described herein may be used to accurately determine orientation, rotation, and relationships of digital images captured in a given space or field of view (FOV) for purposes generating one or more panoramic image views. Panoramic or panorama, as referred herein, may be any wide-angle view, wide-ranging view, or otherwise multi-faceted or multi-part view or representation. A panoramic image view may depict or image of a physical space, environment, or otherwise target feature object or object(s) as a panorama.

For example, in at least in one application and when using a conventional image capture device, such as an intraoral camera alone, to capture digital images of an oral area or cavity, due to the limited space in the oral area or cavity, and limitations of intraoral camera resolution, the FOV can be quite limiting, usually reserved to a few teeth (e.g., usually 2-3) only. It is therefore very difficult for a user or machine vision application to analyze or understand the digital image or the oral area or cavity as captured by the intra oral camera, e.g., for the determination or provision of feedback of oral health. This can be especially problematic for digital images containing oral features because there are generally not many textures or features on the teeth that are depicted in a standard image. In addition, some teeth, as depicted in a standard digital image, may be glossy, contain saliva/drool, or otherwise have some reflective lighting in certain areas or spots within the digital image. Still further, digital images depicting an oral area may contain only teeth, gums, or oral background areas, that provide little information for analyzing or understanding the oral application area (e.g., a user's mouth) based on the images as captured by a conventional imaging device. In addition, images that are small in size may be incorrectly double counted causing faulty image analysis.

The digital image stitching systems and methods described herein, however, synchronizes or otherwise use sensor data (e.g., which may come from multiple and/or different sensor types) to correct the rotation angle first, and then reconstruct individually captured 2D images to generate a 2D panorama view, all without reliance on 3D data as captured from a 3D camera, for example, as would be required by a 3D depth camera or 3D scanner. For example, the digital image stitching systems and methods described herein improve over prior art methods by using both camera information (e.g., digital images) and sensors, e.g., an inertial measurement unit (IMU) and related motion data, each comprising different data types that may be used for machine vision purposes to correctly orient, rotate, and/or stich together images for providing an accurate wider FOV in a given application areas.

For an oral application, by way of non-limiting example, an intraoral camera associated with an IMU sensor may be used to capture limited FOV images. By stitching of these limited images, with rotational correction of the IMU sensor data, a 2D panoramic image view may be reconstructed from the original limited images. In addition, the moving distance of the intraoral camera device may be calculated and stored, thereby providing the machine vision application, or user viewing the 2D panoramic image, much more precise feedback on the progress or movement of the camera scanning in 3D space. Together, the camera and IMU, and tracking of data of each, improve the prediction results of a position model, which may be used to detect, determine, or track objects in the 2D panoramic image. The position model or otherwise 2D panoramic image can be used for various end use applications, such determining zones of an application areas (e.g., a mouth). Still further, the position model or otherwise 2D panoramic image can be further used to focus on specific areas of an application, for example, defining precision from a zonal level to tooth level, and also one or more location(s) of oral issues related to a user's mouth, including at the tooth level or otherwise the user's mouth as a whole.

In addition, in various aspects, multiple position models or otherwise 2D panoramic images may be tracked over time to determine changes at specific locations (common locations) detected within multiple images over a period of time.

For example, with respect to an oral application, multiple position models or otherwise 2D panoramic images may be used to track the evolution of hard tissue (e.g., teeth) and soft tissue (e.g., gums, tongue, cheek) and related issues such as staining, swelling, loss, tartar, wear, salivary calculus, mismatch, and other issues over time for a user's mouth. In addition, the position model or otherwise 2D panoramic image may be used to reconstruct application areas, such as entire rows of teeth image, and abstract the scan/brush path to in order to uniquely identify an individual based on tooth pattern or moth cavity, etc.

Still further, a generated or constructed 2D panorama image may be used to provide user feedback or guidance, for example, on a graphic user interface (GUI) or otherwise display screen, including any of the 2D panorama image itself or data or information determined therefrom or related therein. It is to be understood that an oral application area is but one application area type and that other application areas, as described herein, may be used as well.

More specifically, as described herein, a digital image stitching method is disclosed for generating one or more panoramic image views. The digital image stitching method may comprise capturing, by a camera of a scanner device, a plurality of digital images depicting a target feature within an application area. The plurality of digital images may include at least a first image and a second image. The digital image stitching method may further comprise capturing, by a sensor coupled to the scanner device, motion data as the scanner device moves relative to the target feature. The digital image stitching method may further comprise determining relative position data based on the motion data. The relative position data may include at least first position data corresponding to the first image and second position data corresponding to the second image. The digital image stitching method may further comprise generating, based on the relative position data, at least one of an angle or a position of the second image relative to the first image. The digital image stitching method may further comprise generating, based on image matching of the second image with the first image based on the angle or the position of the second image, a panoramic image view depicting the target feature in a wider field of view of the application area than either the first image or the second image.

In addition, as described herein, a digital image stitching system is disclosed. The digital image stitching system is configured to generate one or more panoramic image views. The digital image stitching system may comprise a scanner device including a camera configured to capture digital images. The digital image stitching system may further comprise a sensor coupled to the scanner device and configured to capture motion data. The digital image stitching system may further comprise one or more processors communicatively coupled to the scanner device. The digital image stitching system may further comprise a computer readable medium storing computing instructions configured to execute on the one or more processors. The computing instructions, when executed by the one or more processors, may cause the one or more processors to capture, by the camera, a plurality of digital images depicting a target feature within an application area. The plurality of digital images may comprise at least a first image and a second image. The computing instructions, when executed by the one or more processors, may further cause the one or more processors to capture, by the sensor, the motion data as the scanner device moves relative to the target feature. The computing instructions, when executed by the one or more processors, may further cause the one or more processors to determine relative position data based on the motion data. The relative position data may include at least first position data corresponding to the first image and second position data corresponding to the second image. The computing instructions, when executed by the one or more processors, may further cause the one or more processors to generate, based on the relative position data, at least one of an angle or a position of the second image relative to the first image. The computing instructions, when executed by the one or more processors, may further cause the one or more processors to generate, based on image matching of the second image with the first image based on the angle or the position of the second image, a panoramic image view depicting the target feature in a wider field of view of the application area than either the first image or the second image.

Further, as described herein, a tangible, non-transitory computer-readable medium storing instructions for generating one or more panoramic image views is disclosed. The instructions, when executed by one or more processors, may cause the one or more processors to capture, by a camera of a scanner device, a plurality of digital images depicting a target feature within an application area. The plurality of digital images may include at least a first image and a second image. The instructions, when executed by one or more processors, may further cause the one or more processors to capture, by a sensor coupled to the scanner device, motion data as the scanner device moves relative to the target feature. The instructions, when executed by one or more processors, may further cause the one or more processors to determine relative position data based on the motion data. The relative position data may include at least first position data corresponding to the first image and second position data corresponding to the second image. The instructions, when executed by one or more processors, may further cause the one or more processors to generate, based on the relative position data, at least one of an angle or a position of the second image relative to the first image. The instructions, when executed by one or more processors, may further cause the one or more processors to generate, based on image matching of the second image with the first image based on the angle or the position of the second image, a panoramic image view depicting the target feature in a wider field of view of the application area than either the first image or the second image.

The present disclosure relates to improvements to other technologies or technical fields at least because the present disclosure describes or introduces improvements to computing devices in the digital imaging field, whereby digital image stitching systems and methods execute by use of scanner device(s) or computing devices and improves the field of digital imaging manipulation by generating more accurate, corrected, or otherwise enhanced panoramic image view(s) via rotation based on sensor data to improve the precision of template matching on a digital image frame-by-frame basis. Accordingly, the digital images, e.g., panoramic image view(s), generated by the disclosed systems and methods allow for more accurate images that can be used in a variety of end purposes, such as oral treatment or otherwise as described herein.

Still further, the present disclosure relates to improvement to other technologies or technical fields at least because the present disclosure describes or introduces improvements to computing devices in the field of security and/or image processing, where, at least in some aspects, scanner behaviors of users may be determined to uniquely identify users without depicting personal identifiable information (PII) of a given user. By using the systems and methods described herein, a scan behavior can be abstracted from any detailed PII. Such features provide a security improvement, i.e., where the removal of PII (e.g., private area features) provides an improvement over prior systems that require images of the user, especially ones that may be transmitted over a network (e.g., the Internet). Accordingly, the systems and methods described herein operate without the need for such essential information, which provides an improvement, e.g., a security improvement, over prior systems. In addition, the use of scan behavior patterns, at least in some aspects, allows the underlying system to store and/or process fewer (or in some cases no) digital images, which results in a performance increase to the underlying system as a whole because the fewer images require less storage memory and/or processing resources to store, process, and/or otherwise manipulate by the underlying computer system.

Still further, the present disclosure includes applying certain of the claim elements with, or by use of, a particular machine, e.g., a scanner device, which may comprise a intraoral device with a camera for capturing images of a user's mouth and a sensor coupled to the scanner device for capturing motion data that is relative to, or that corresponds to, the image data.

In addition, the present disclosure includes specific features other than what is well-understood, routine, conventional activity in the field, and that add unconventional steps that confine the claim to a particular useful application, e.g., digital image stitching method for generating one or more panoramic image views.

Advantages will become more apparent to those of ordinary skill in the art from the following description of the preferred aspects which have been shown and described by way of illustration. As will be realized, the present aspects may be capable of other and different aspects, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts a particular aspect of the disclosed system and methods, and that each of the Figures is intended to accord with a possible aspect thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present aspects are not limited to the precise arrangements and instrumentalities shown, wherein.

The Figures depict preferred aspects for purposes of illustration only. Alternative aspects of the systems and methods illustrated herein may be employed without departing from the principles of the invention described herein.

DETAILED DESCRIPTION OF THE INVENTION

Figure 1:
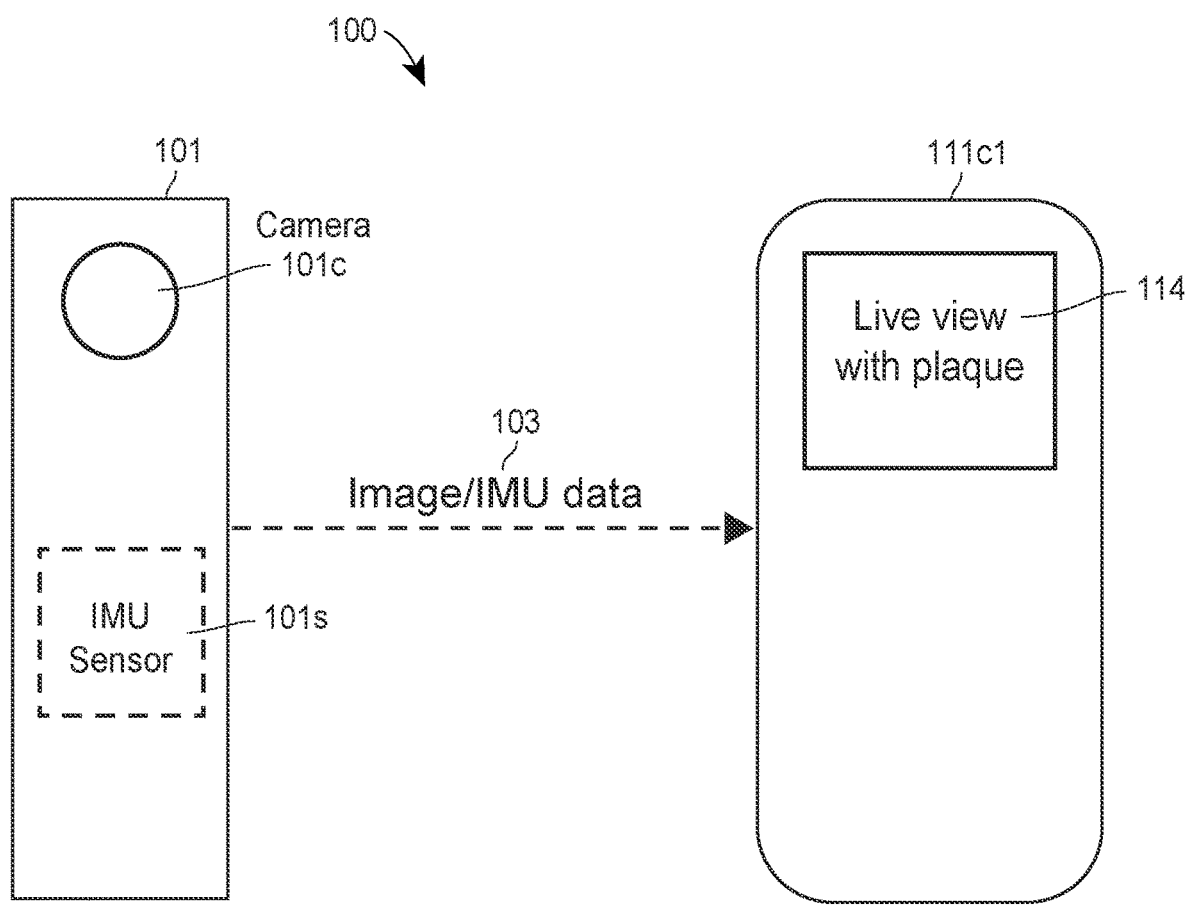
FIG. 1 illustrates an example digital image stitching system, in accordance with various aspects disclosed herein.

FIG. 1 illustrates an example digital image stitching system 100, in accordance with various aspects disclosed herein. As shown for FIG. 1, digital image stitching system 100 comprises a scanner device 101. In various aspects, scanner device 101 may comprise a hand-held device or a clip-on device. For example, in some aspects, the scanner device may be configured to be held in a user's hand. Additionally, or alternatively, scanner device 101 may clip on, or otherwise attach to, a device or apparatus, such as a tooth brush or cleaning apparatus, for movement or positions by an end user.

Scanner device 101 comprises a camera 101c configured to capture digital images. The camera may be configured for various different purposes, and thus, be configured to capture digital images at various different zoom levels, digital resolutions, or quality based on the application for which camera 101c is used. For example, in aspects comprising oral applications, camera 101c may comprise an intraoral camera and/or a hyperspectral camera. In still further aspects, the camera may be embedded within, at least partially contained by, or otherwise part of or coupled to an oral device or oral treatment device, e.g., such as a toothbrush or a mouth piece, which may contain one or more cameras for capturing images at different positions for image stitching as described herein. Further, for application involving a cleaning device for cleaning a surface, such as floor, camera 101c may comprise a floor camera configured to be angled toward the ground and for imaging a surface (e.g., the floor) as the camera moves along the surface. Still further, for applications involving human skin or tissue, the camera may comprise a skin camera capable of capturing digital images having a high resolution or high definition for detailing aspects of human skin, such as follicles, pores, or the like. In some aspects, scanner device 101 may comprise a physical distancing element, which may be an attachment or a shroud physically coupled to the scanner device. The physical distancing element (e.g., shroud) is configured to maintain a constant distance (e.g., 1-10 millimeters) between the camera (e.g., camera 101c) and a target feature and/or an application area being imaged by the camera. For example, the physical distancing element may be attached to the scanner device where the user places the physical distancing element portion of the scanner device on, or within a proximity to, the user as the scanner moves relative to the user. It is to be understood, however, that other uses or configurations of the physical distancing element may be used in order to maintain a constant distance between the camera (e.g., camera 101c) and a target feature and/or an application area being imaged by the camera.

Digital images, as captured by camera 101c, may comprise pixel data (e.g., RGB data) comprising feature data and corresponding to one or more image features, within the respective image. The digital images may comprise pixel data. With respect to digital images as described herein, pixel data may comprise individual points or squares of data within an image, where each point or square represents a single pixel within an image. Each pixel may be at a specific location within an image. In addition, each pixel may have a specific color (or lack thereof). Pixel color, may be determined by a color format and related channel data associated with a given pixel. For example, a popular color format is a 1976 CIELAB (also referenced herein as the "CIE L*-a*-b*" or simply "L*a*b*" or "LAB" color format) color format that is configured to mimic the human perception of color. Namely, the L*a*b* color format is designed such that the amount of numerical change in the three values representing the L*a*b* color format (e.g., L*, a*, and b*) corresponds roughly to the same amount of visually perceived change by a human. This color format is advantageous, for example, because the L*a*b* gamut (e.g., the complete subset of colors included as part of the color format) includes both the gamuts of Red (R), Green (G), and Blue (B) (collectively RGB) and Cyan (C), Magenta (M), Yellow (Y), and Black (K) (collectively CMYK) color formats.

In the L*a*b* color format, color is viewed as point in three dimensional space, as defined by the three-dimensional coordinate system (L*, a*, b*), where each of the L* data, the a* data, and the b* data may correspond to individual color channels, and may therefore be referenced as channel data. In this three-dimensional coordinate system, the L* axis describes the brightness (luminance) of the color with values from 0 (black) to 100 (white). The a* axis describes the green or red ratio of a color with positive a* values (+a*) indicating red hue and negative a* values (−a*) indicating green hue. The b* axis describes the blue or yellow ratio of a color with positive b* values (+b*) indicating yellow hue and negative b* values (−b*) indicating blue hue. Generally, the values corresponding to the a* and b* axes may be unbounded, such that the a* and b* axes may include any suitable numerical values to express the axis boundaries. However, the a* and b* axes may typically include lower and upper boundaries that range from approximately 150 to −150. Thus, in this manner, each pixel color value may be represented as a three-tuple of the L*, a*, and b* values to create a final color for a given pixel.

As another example, an additional or alternative color format includes the red-green-blue (RGB) format having red, green, and blue channels. That is, in the RGB format, data of a pixel is represented by three numerical RGB components (Red, Green, Blue), that may be referred to as a channel data, to manipulate the color of a pixel's area within the image. In some implementations, the three RGB components may be represented as three 8-bit numbers for each pixel. Three 8-bit bytes (one byte for each of RGB) may be used to generate 24-bit color. Each 8-bit RGB component can have 256 possible values, ranging from 0 to 255 (i.e., in the base 2 binary system, an 8-bit byte can contain one of 256 numeric values ranging from 0 to 255). This channel data (R, G, and B) can be assigned a value from 0 to 255 that can be used to set the pixel's color. For example, three values like (250, 165, 0), meaning (Red=250, Green=165, Blue=0), can denote one Orange pixel. As a further example, (Red=255, Green=255, Blue=0) means Red and Green, each fully saturated (255 is as bright as 8 bits can be), with no Blue (zero), with the resulting color being Yellow. As a still further example, the color black has an RGB value of (Red=0, Green=0, Blue=0) and white has an RGB value of (Red=255, Green=255, Blue=255). Gray has the property of having equal or similar RGB values, for example, (Red=220, Green=220, Blue=220) is a light gray (near white), and (Red=40, Green=40, Blue=40) is a dark gray (near black).

In this way, the composite of three RGB values creates a final color for a given pixel. With a 24-bit RGB color image, using 3 bytes to define a color, there can be 256 shades of red, and 256 shades of green, and 256 shades of blue. This provides 256×256×256, i.e., 16.7 million possible combinations or colors for 24 bit RGB color images. As such, a pixel's RGB data value indicates a degree of color or light each of a Red, a Green, and a Blue pixel is comprised of. The three colors, and their intensity levels, are combined at that image pixel, i.e., at that pixel location on a display screen, to illuminate a display screen at that location with that color. In is to be understood, however, that other bit sizes, having fewer or more bits, e.g., 10-bits, may be used to result in fewer or more overall colors and ranges. Further, it is to be understood that the pixel data may contain additional or alternative color format and channel data. For example, the pixel data may include color data expressed in a hue saturation value (HSV) format or hue saturation lightness (HSL) format.

As a whole, the various pixels, positioned together in a grid pattern, form a digital image or portion thereof. A single digital image can comprise thousands or millions of pixels or channels. Images can be captured, generated, stored, and/or transmitted in a number of formats, such as JPEG, TIFF, PNG and GIF. These formats use pixels to store or represent the image. The images may be stored on a memory of scanner device 101 and/or a mobile device 111c1, or other electronic or digital storage as described herein. Manipulation of images, and pixel data, for example, via image stitching is further described herein with respect to FIGS. 2-4, or otherwise as described herein.

With reference to FIG. 1, scanner device 101 further comprises a sensor 101s coupled to the scanner device 101 and configured to capture motion data. In various aspects, the sensor may comprise one or more of: a gyroscope, an accelerator, a magnetic sensor, or an inertial measurement unit (IMU). In the example of FIG. 1, sensor 101s comprise an IMU sensor for capturing motion data as the scanner device moves in space.

Scanner device 101 further comprises one or more processors communicatively coupled to scanner device 101. The one or more processors may initiate the capture of the images and motion data or otherwise sensor data. The one or more processors may also receive the digital images, as captured by camera 101*c*, and the motion data as captured by sensor 101*s*. The one or more processors may be processors on scanner device 101 itself. Additionally, or alternatively, the one or more processors may be processors of a computing device remote to scanner device 101, such as mobile device 111*c*1, or a server (for example, see FIG. 12 herein), that scanner device 101 is communicatively coupled to. In this way the one or more processors may include a processor on scanner device 101 itself and a processor remote to scanner device 101 such that the digital image stitching system 100 can have one or more processors that interact with each other.

As shown for FIG. 1, scanner device 101 may include a wireless component (not shown), such as a wireless component (e.g., system on a chip (SOC) or otherwise circuit) implementing the 802.11 (WI/FI) communication standard or the BLUETOOTH communication standard. The wireless component may connect to otherwise communicate with mobile device 111*c*1 or a hub (not shown) configured to communicate with the scanner device. Mobile device 111*c*1 or the hub (not shown) may comprise an APPLE IOS based device or a GOOGLE ANDROID device, such as an APPLE IPHONE, a GOOGLE ANDROID based phone, or a proprietary device (e.g., the hub) configured for communication with scanner device 101. For example, the hub may implement a separate BIOS and/or operating system for communication (e.g., wired or wireless) with the scanner device 101. As further described herein (e.g., for FIG. 12), mobile device 111*c*1 or hub (not shown) may implement or execute a panoramic imaging application (app) 108, which may comprise a native app operating on a mobile operating system of mobile device 111*c*1 or the hub. In various aspects, scanner device 101 may transmit digital images and sensor data (e.g., IMU data) via the wireless component for analysis and/or display by a display screen and/or graphics user interface (GUI) on mobile device 111*c*1 or hub. In additional aspects, image stitching, as described by the digital imaging stitching systems and methods herein, may be performed entirely by the scanner device 101, without the need to communicate with a mobile device or a hub. That is, it is to be understood that, at least in some aspects, the digital imaging stitching systems and methods as implemented herein may be implemented on a device that contains each of the hardware and software components (e.g., camera 101*c*, sensor 101*s*, processors, panoramic imaging app 108, etc.) as described for FIGS. 1 and 2, or otherwise shown or described herein.

In the example aspect of FIG. 1, scanner device may comprise an oral scanner device or an intraoral device to capture oral images in an oral application area, where the oral images and related motion data, as captured when the scanner device is moved, may be transmitted wirelessly to mobile device 111*c*1. Panoramic imaging 108 may display a live view of the oral images, as one or more panoramic image views as described herein, where the panoramic images view(s) may indicate or otherwise show plaque buildup on teeth of a user, plaque location, change in remaining plaque, and/or similar related features.

It is to be understood, however, that at least in some aspects, scanner device 101 may comprise, more generally, a non-oral scanning device that captures images and data for non-oral purposes, for example, as described for certain aspects herein.

Figure 2:
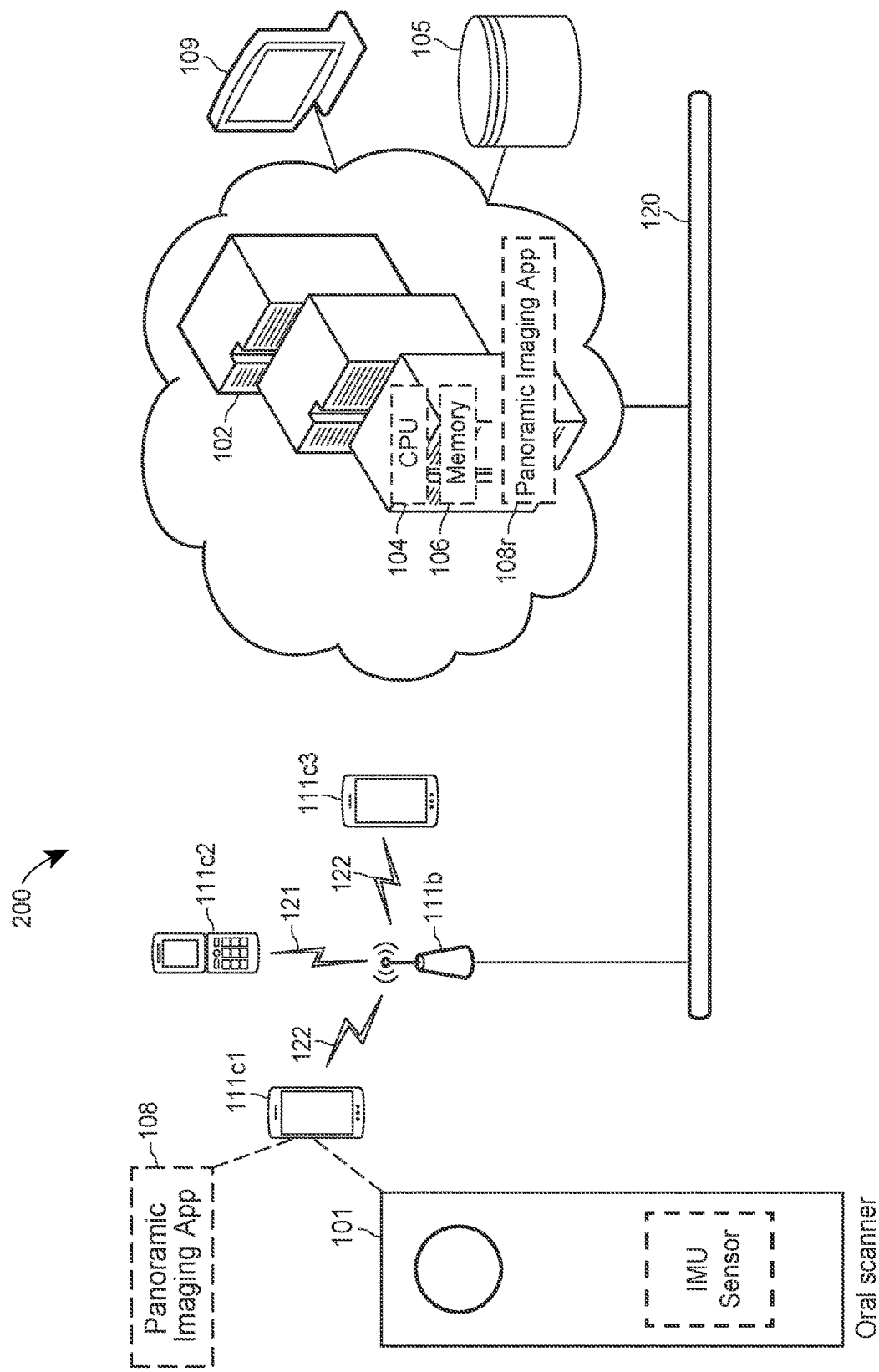
FIG. 2 illustrates an example network diagram for the digital image stitching system of FIG. 1 in accordance with various aspects disclosed herein.

Each of scanner device 101 and mobile device 111*c*1 may further comprise a computer readable medium (e.g., computer memory) storing computing instructions configured to execute on one or more processors, wherein the computing instructions, when executed by the one or more processors, cause the one or more processors to implement a digital image stitching algorithm, such as the digital image stitching method illustrated and described for FIG. 2, or as otherwise described herein. In various aspects the computer readable medium may comprise a tangible, non-transitory computer-readable medium, such as a RAM, ROM, or other forms of electronic or digital memory for storage of computing instructions. The computer medium can be memory of a mobile phone, hub, and/or server (e.g., cloud system), or combination therefor, and can be used for storing digital images and motion data, but also but also for storing computing instructions implemented by the one or more processors of the digital image stitching system 100.

FIG. 2 illustrates an example network diagram 200 for the digital image stitching system 100 of FIG. 1, in accordance with various aspects disclosed herein. As shown for network diagram 200, digital image stitching system 100 may further comprise remote server(s) 102 that communicate with mobile device 111*c*1 via a computer network. As shown for FIG. 2, digital image stitching system 100 may comprise processors and/or memories, such as processors and or memories of a server or cloud computing platform that communicate with scanner device 101 remotely, such as over a computer network such as the Internet. In some aspects, communication with scanner device 101 may communicate directly with server(s) 102. Additionally, or alternatively, scanner device 101 may communicate with scanner device 101 through mobile device 111*c*1. For example, in various aspects digital image stitching system 100 may comprise one or more servers 102, which may comprise multiple, redundant, or replicated servers as part of a server farm. In still further aspects, such server(s) 102 may be implemented as cloud-based servers, such as a cloud-based computing platform. For example, the server(s) 102 may be any one or more cloud-based platform(s) such as MICROSOFT AZURE, AMAZON AWS, or the like. The server(s) may include one or more processors (e.g., CPU 104) as well as one or more computer memories (e.g., memory 106). Memories may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Memories may store an operating system (OS) (e.g., MICROSOFT WINDOWS, LINUX, UNIX, etc.) capable of facilitating the functionalities, apps, methods, or other software as discussed herein. Memories (e.g., memory 106) may also store a panoramic imaging application (app) 108*r*, which may comprise computing instructions as described herein for generating one or more panoramic image views as described herein. Panoramic imaging app 108*r* may comprise at least a portion, such as a remote portion, of the computing instructions, where a remaining or local portion (e.g., panoramic imaging app 108 implemented on mobile device 111*c*1) executes in communication with app 108*r* across a computer network 120.

Server(s) 102 may further include a communication component configured to communicate (e.g., send and receive) data via one or more external/network port(s) to one or more networks or local terminals, such as computer network 120 and/or terminal 109 (for accessing digital images or motion data) described herein. In some embodiments, imaging server(s) 102 may include a client-server platform technology such as ASP.NET, Java J2EE, Ruby on Rails, Node.js, a web service or online API, responsive for receiving and responding to electronic requests. Server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein.

Server(s) 102 may also be communicatively coupled to database 105, which may store digital images, motion data, and/or other data, including digital images and motion data as captured by scanner device 101, as described herein. Such digital images, motion data, and/or other data as described herein may be transmitted between app 108 and app 108r, where app 108r can store and/or access such information to and from memory 106 and/or database 105. Memories (e.g., memory 106) may store machine readable instructions, including any of one or more application(s) (e.g., app 108r comprising a set of computing instructions as described herein), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be configured to facilitate their various functionalities discussed herein. It should be appreciated that one or more other applications may be envisioned and that may be executed by the processor(s) (e.g., CPU 104).

In addition, the one or more processors (e.g., CPU 104) as described herein may be connected to the memories (e.g., memory 106) via a computer bus responsible for transmitting and/or receiving electronic data, data packets, or otherwise electronic signals to and from the processor(s) and memories in order to implement or perform the machine readable instructions, methods, processes, elements or limitations, as illustrated, depicted, or described for the various flowcharts, illustrations, diagrams, figures, and/or other disclosure herein. One or more processor(s) (e.g., CPU 104) may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120. In some aspects, the computer network 120 may comprise a private network or local area network (LAN). Additionally, or alternatively, the computer network may comprise a public network such as the Internet.

Server(s) 102 may further include or implement an operator interface configured to present information to an administrator or operator and/or receive inputs from the administrator or operator. As shown in FIG. 2, an operator interface may provide a display screen (e.g., via terminal 109). Server(s) 102 may also provide I/O components (e.g., ports, capacitive or resistive touch sensitive input panels, keys, buttons, lights, LEDs), which may be directly accessible via, or attached to, server(s) 102 or may be indirectly accessible via or attached to terminal 109. According to some embodiments, an administrator or operator may access the server 102 via terminal 109 to review information, make changes, input data, and/or perform other functions.

As described herein, in some embodiments, server(s) 102 may perform the functionalities as discussed herein as part of a "cloud" network or may otherwise communicate with other hardware or software components within the cloud to send, retrieve, or otherwise analyze data or information described herein, including communication between apps 108 and 108r.

In general, a computer program or computer based product, application (app), or code (e.g., computing instructions or software of the scanner device 101, panoramic imaging app 108, or otherwise of the digital image stitching systems and methods described herein) may be stored on a computer usable storage medium, or tangible, non-transitory computer-readable medium (e.g., random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) and/or processors of mobile devices (e.g., mobile device 111c1) (e.g., working in connection with the respective operating system) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C #, Objective-C, Java, Scala, ActionScript, JavaScript, HTML, CSS, XML, etc.).

As shown in FIG. 2, server(s) 102 are communicatively connected, via computer network 120 to mobile device 111c1 via base station 111b. In some embodiments, base station 111b comprises a cellular base station, such as a cell tower, communicating to mobile device 111c1 via wireless communication 122 based on any one or more of various mobile phone standards, including NMT, GSM, CDMA, UMMTS, LTE, 5G, or the like. Additionally, or alternatively, base station 111b may comprise routers, wireless switches, or other such wireless connection points communicating to mobile device 111c1 via wireless communication 121 based on any one or more of various wireless standards, including by non-limiting example, IEEE 802.11a/b/c/g (WIFI), the BLUETOOTH standard, or the like.

Mobile device 111c1 may comprise a mobile devices and/or client device for accessing and/or communications with server(s) 102. Such mobile devices may comprise one or more mobile processor(s). In various embodiments, mobile device 111c1 comprises a mobile phone (e.g., a cellular phone), a tablet device, a personal data assistance (PDA), or the like, including, by non-limiting example, an APPLE iPhone or iPad device or a GOOGLE ANDROID based mobile phone or table. Mobile device 111c1 may communicate directly (e.g., via wireless communication 422, such as WIFI or BLUETOOTH) with scanner device 101. Additionally, or alternatively, scanner device 101 may communicate directly with base station 111b via wireless communication, such as such as WIFI or BLUETOOTH. In this way, wireless connectivity among mobile device 111c1, scanner device 101, and/or base station 111b provides communication between scanner device 101, mobile device 111c1, and server(s) 102 for sending and receiving data, such as digital images and/or motion data for generating one or more panoramic image views a described herein.

Figure 3:
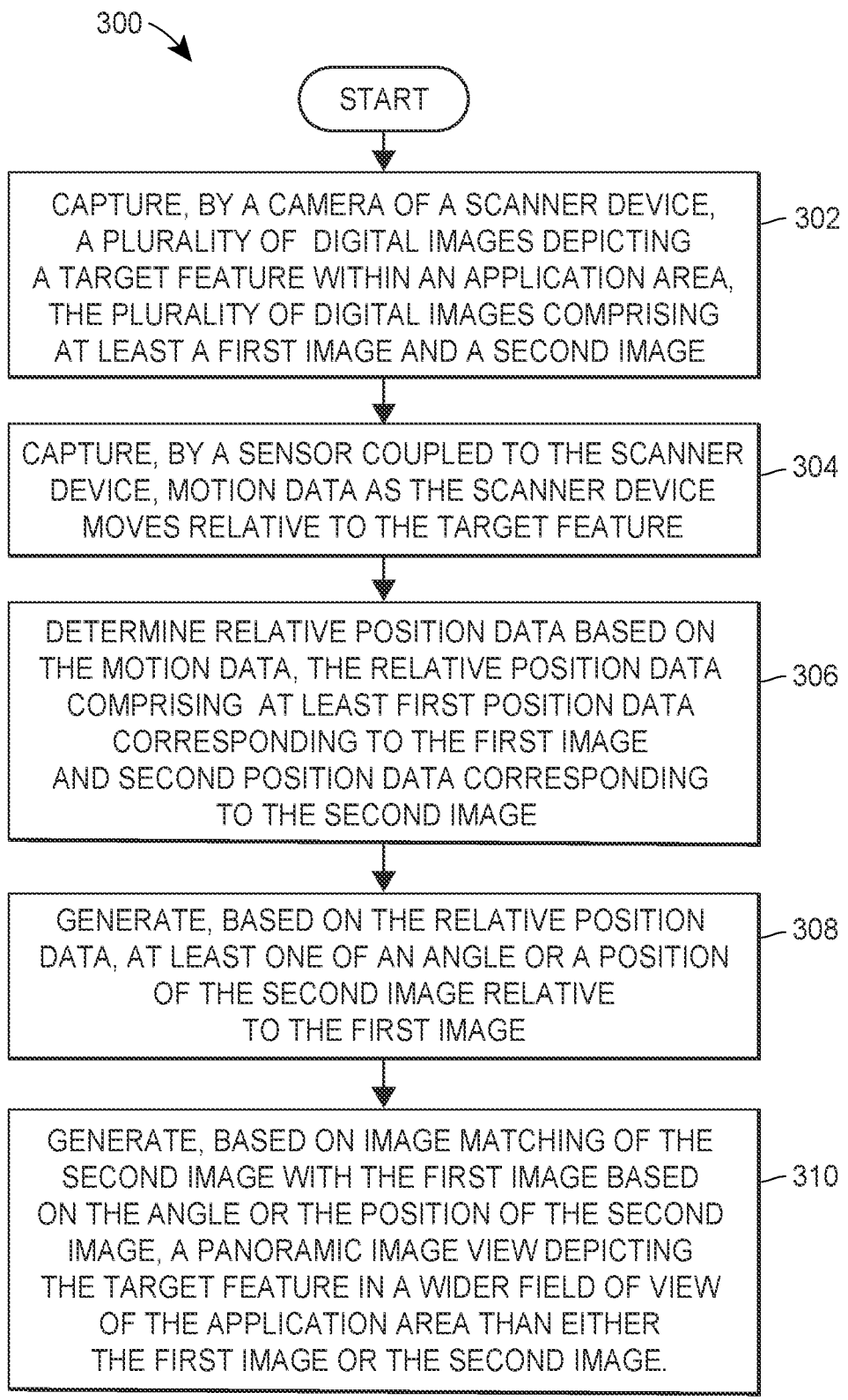
FIG. 3 illustrates an example digital image stitching method, in accordance with various aspects disclosed herein.

With reference to FIGS. 1 and 2, it is to be understood that additional or alternative configurations and/or positions of the scanner device 101, mobile device 111c1, processor(s), and/or memories of digital image stitching system 100 are contemplated herein such that these components are configured and/or positioned so as to be electronically and communicatively coupled with respect to one another for digital image stitching for generating one or more panoramic image views, in accordance with various aspects disclosed herein FIG. 3 illustrates an example digital image stitching method 300, in accordance with various aspects disclosed herein. At block 302 digital image stitching method 300 comprises capturing, by a camera (e.g., camera 101c) of a scanner device (e.g., scanner device 101), a plurality of digital images depicting a target feature within an application area. In some aspects, the application area may be an oral area, such as a mouth of a user comprising teeth, gums, and the like, for example as described in FIGS. 4-11 herein. In other aspects, the application area may be a skin area, e.g., a face area or a body area regarding face or body cleaning or washing. In still further aspects, the application area may be a floor area, such as a hardwood floor, carpeted floor, in which the application may comprise cleaning with a cleaning device.

More generally, the plurality of digital images may comprise at least a first image and a second image as captured by the camera (e.g., camera 101c). The first image and second image may be frames of a several digital captured in a sequence, e.g., for a video as captured by the camera (e.g., camera 101c). First image and second image may be referred to herein as frame to (e.g., captured at a first time) and frame $t_1$ (e.g., captured at a second time), respectively. It is to be understood that frame $t_0$ and $t_1$ need not be consecutive frames in a set of image frames (e.g., as a video comprising a set of image frames). That is, in some aspects, frames $t_0$ and $t_1$ may be frames that are separated by one or more intermediary frames, for example, where $t_0$ is a first frame in a set of image frames or video, but where and $t_1$ is a third frame, or a seventh frame, or some other frame that is non-consecutive with respect to frame to in the set of image frames or video. In an additional aspect, an image may be dropped, deleted, or otherwise not used in generating the panoramic image view if such image it falls below a quality criterion. For example, the quality criterion may comprise image sharpness or resolution. More specifically, in such aspects, the plurality of images as captured by the camera may comprise a third image. The digital image stitching method 300 may include determining that the third image lacks a quality criterion (e.g., sharpness), which may require a threshold value in ordered to be fulfilled (e.g., a threshold level of sharpness may be required to use the third image). The digital image stitching method may discard the third image from use in generating the panoramic image view where third image falls below the threshold value or otherwise quality criterion.

In some aspects, the target feature (e.g., a tooth for an oral application area) may be detected within the application area before the plurality of images are captured. That is, in some aspects, the target feature may be automatically detected within the application area which causes the plurality of images to be captured. In such aspects, the targeted featured may be detected and/or sensed in the application whereby, for example, one or more pixels of preliminary digital images comprising the targeted feature is detected by the camera (e.g., camera 101c) before the digital images (e.g., the first image and the second image) are captured by the camera. Additionally, or alternatively, motion of sensor 101s, which may be detected from moving scanner device 101 in a unique way, may initiate captured of the digital images and/or motion data.

At block 304 digital image stitching method 300 comprises capturing, by a sensor (e.g., sensor 101s) coupled to the scanner device, motion data as the scanner device moves relative to the target feature. In various aspects, the sensor may be an inertial measurement unit (IMU). An IMU may comprise one or more of an accelerometer configured to measure velocity and/or acceleration, a gyroscope configured to measure rotation and/or rotational rate, and/or a magnetometer configured to measure or establish a cardinal direction (e.g., directional heading), etc.

At block 306 digital image stitching method 300 comprises determining relative position data based on the motion data. The relative position data may comprise at least first position data corresponding to the first image and second position data corresponding to the second image. The relative position data may define a movement from a first position to a second position, which may correspond to movement of the scanner device (e.g., scanner device 101) as the camera (e.g., camera 101c) capture first image and second image. It is to be understood that position data (e.g., relative position data, first position data, or second position data) may comprise sensor data such as accelerometer data or other such motion data, e.g., as captured by a sensor (e.g., sensor 101s) of the scanner device (e.g., scanner device 101), which may be, for example, data as captured by a gyroscope, an accelerator, a magnetic sensor, or an inertial measurement unit (IMU), or other such sensor device.

At block 308 digital image stitching method 300 comprises generating, based on the relative position data, at least one of an angle or a position of the second image relative to the first image. In some aspects, generation of the angle or the position of the second image may include adjusting the angle or position of the second image relative to the first image.

At block 310 digital image stitching method 300 comprises generating, based on image matching of the second image with the first image based on the angle or the position of the second image, a panoramic image view depicting the target feature in a wider field of view of the application area than either the first image or the second image. For example, and as further described herein for FIG. 4, a template matching algorithm or otherwise digital image stitching algorithm may be applied the target feature identifiable in or depicted within the captured digital images (e.g., the first image and the second image) after rotation and/or positioning of the images with the motion data of the sensor (e.g., IMU sensor signal data). In various aspects, the panoramic image view may comprise a digital image that can be a new digital image generated, such as rasterized or vectored, from the plurality of digital images. Additionally, or alternatively, the panoramic image view may be a view comprising the original digital images positioned next to one another (but still maintained as separate images) according to the digital image stitching method. In such aspects, the data or attributes (e.g., position, angle of rotation, etc.) of the original images may be maintained. Additionally, or alternatively, and as further described for FIG. 7 herein, a distance may be determined or generated that defines a distance from the first image to the second image, or even a distance for a plurality of digital images, based on the image matching of the second image with the first image based on the angle or the position of the second image.

In some aspects, digital image stitching method 300 may comprise outputting a control signal based on at least one of the panoramic image view, the plurality of images, or the position data. The control signal may be a wired or wireless control signal that controls an operation of at least the scanning device (e.g., scanner device 101), the camera (e.g., camera 101c), or the sensor (e.g., sensor 101s), and may be provided to alter or configure any of these devices to control the operation of digital image or sensor data capture or otherwise operation of these devices.

Figure 4:
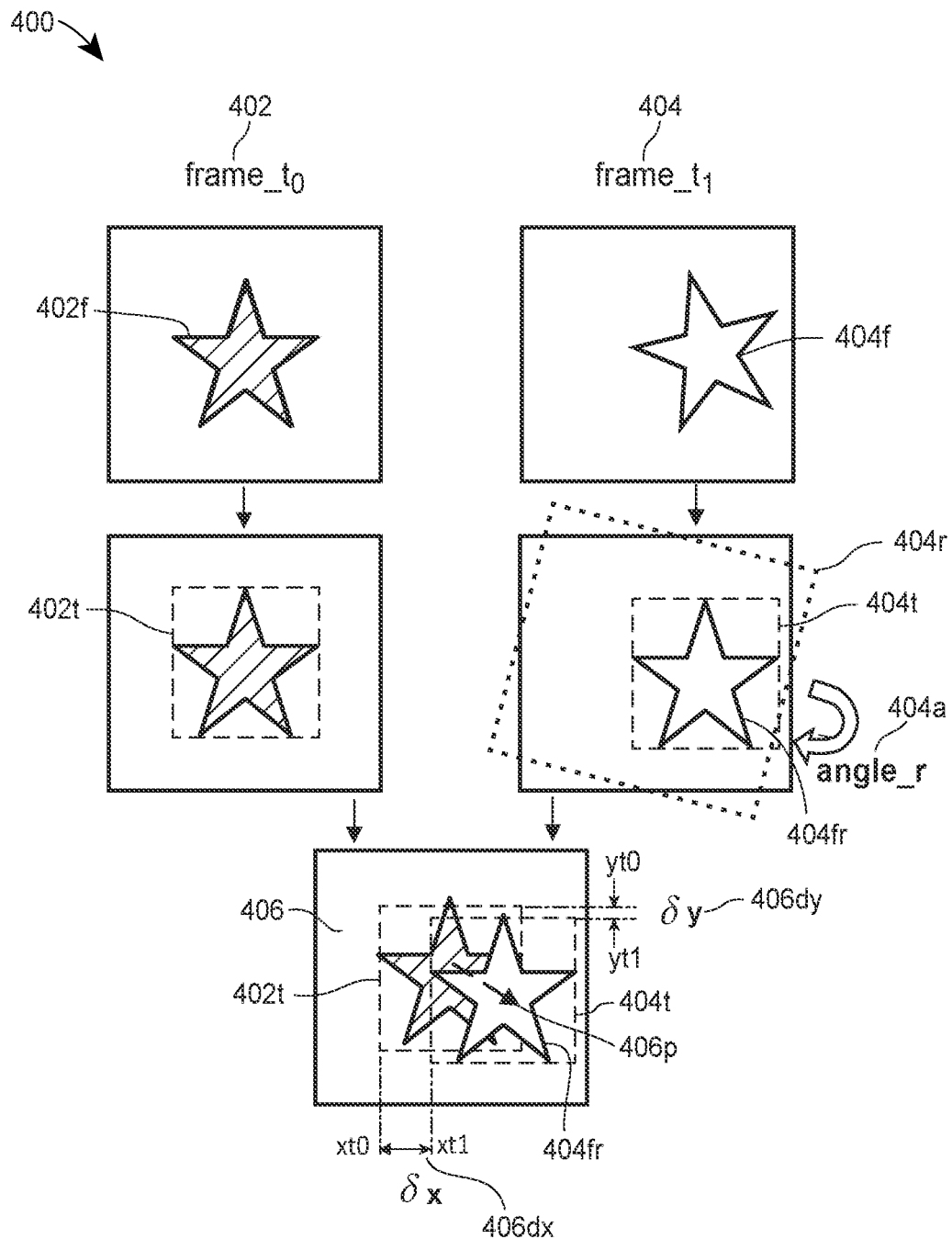
FIG. 4 illustrates an example digital image stitching algorithm in accordance with various aspects disclosed herein.

FIG. 4 illustrates an example digital image stitching algorithm 400 in accordance with various aspects disclosed herein. Digital image stitching algorithm 400 may be utilized by example digital image stitching method 300 as described herein.

Each of the images (e.g., digital images 402 and 404) of FIG. 4 may comprise a plurality of pixels. The pixel data, and features thereof, may define the target feature (e.g., target feature 402f) in the image. For example, pixels may define features determined from or otherwise based on one or more pixels in a digital image. For example, target feature 404f may define pixels comprising a darker pixel color (e.g., pixels with relatively low L* values and/or pixels with lower RGB values) that are indicative of given feature(s) of the image. For example, groups of pixels, of similar colors and locations can represent features of the image. Additionally, or alternatively, a collection of surface edges can be used to determine an outline of a target feature in the image, and the position of those edges relative to other parts of the image can be used to determine the perimeter or otherwise shape of the target feature within the image. Still further, a center pixel or center pixels may be determined of a respective image. Any of the center pixel(s), target features, outline, perimeter, or combination thereof may be used by the digital image stitching algorithm to perform template matching and/or to otherwise generate a panoramic image view. In addition, a distance may also be generated based on horizontal and vertical distances of a plurality of images, which is further described herein for FIG. 7.

Generally, generation of an angle (e.g., angle 404a) and/or a position (e.g., position 406p) for a second image (e.g., digital image 404), or otherwise next image in a sequence of images (e.g., video having image frames), can comprise implementing a template matching as executed by digital image stitching algorithm 400. For example, in some aspects, template matching may be provided by an OPENCV, which is an open source software library that provides real-time computer or machine vision tools.

To implement template matching of digital image stitching algorithm 400, a target feature (e.g., target feature 402f) of a first digital image (e.g., digital image 402, which may be a first frame, frame t0, in an image series captured by camera 101c) is identified. The target feature is then identified in the next frame, e.g., digital image 404a, which may be a second frame, frame_$t_1$, in an image series captured by camera 101c. In digital image 404, the target feature 404f is shown as rotated relative to the first image (e.g., digital image 402), where such rotation may have occurred due to movement of camera 101c as scanner device 101 was moved relative to the target feature during image capture. Generally, as used herein, a feature can be recognized as, or may refer to, one or more image feature(s) that correspond to any one or more pixel(s) or group of pixels of an image. Moreover, the image can be an original image, video frame, or any processed image. Still further, a feature can also be recognized as a target feature of interest as selected or determined in an image, where, by non-limiting example, target feature(s) may comprise oral feature(s) such as plaque, calculus, tartar, teeth, gum, or any other oral features as described herein.

More specifically, as shown for FIG. 4, a first area in the first image (e.g., digital image 402) is selected as a template 402t for the target feature 402f. The location of template 402t can be determined or based on a center pixel of the digital image 402 itself and/or one or more pixels of the target feature 402f. An angle 404a can then be determined for a second image (e.g., digital image 404). For example, generating the angle 404a of the second image may comprise determining one or more angular velocity(s) of the sensor (e.g., sensor 101s). For example, this may comprise determining an angular velocity change based on the motion data of the sensor as captured as the scanner device 101 moved relative to the object (e.g., a star as shown for FIG. 4) that comprises the target feature (e.g., star 402o and as shown the first and second images (e.g., digital image 402 and digital image 404). A tilt angle 404a may then be determined for the second image based on the angular velocity change from the first image to the second image. The second image (e.g., digital image 404) may then be rotated (404r) by the tilt angle 404a, thus causing target feature 404f in digital image 404 (which corresponds to target feature 402o to likewise be rotated (e.g., rotated target feature 404fr) relative to the first image. Said another way, the angular velocity change at time t0 at coordinate $(x_0, y_0)$ from the first image to the second image at time $t_1$ at coordinate $(x_1, y_1)$ may be determined from the motion data. In some aspects, the angular velocity change may be used to generate a delta angle (e.g., tilt angle 404a). This delta angle (e.g., tilt angle 404a) may then be used for rotating the second image for orientation with respect to the first image. In this way, correction of the second image via rotation based on sensor data improves the precision of template matching on a frame-by-frame basis.

Once rotated, digital image stitching algorithm 400 can generate a panoramic image view (e.g., panoramic image view 406) from the first image and the second image (as rotated) by positioning the first image and the second image based on the sensor data. For example, generating a position of the second image 404 may comprise determining a first image feature (e.g., a central feature in for a template, e.g., template 402t, or otherwise pixel or group of pixels corresponding to an item depicted in the first image, such as target feature 402o within the first image (e.g., digital image 402), and determining a second image feature (e.g., rotated target feature 404fr) within the second image. The first image feature (e.g., target feature 402o may correspond to the second image feature (e.g., rotated target feature 404fr), where a coordinate distance is determined between the first image feature (e.g., target feature 402o and the second image feature (e.g., rotated target feature 404fr). The coordinate distance may then be used to set the position of the second image as rotated by offsetting the second image from the first image by the coordinate distance. In the example, of FIG. 4 the coordinate distance is comprised of a horizontal distance, i.e., $\delta_x$ (406dx) and a vertical distance, i.e., $\delta_y$ (406dy) such that second image as rotated (404r) is offset by the coordinate distance, formed by both the horizontal distance 406dx and vertical distance 406dy, causing target feature 404fr of template 404t to be both positioned and offset from, and angled relative to, target feature 402f of template 402t, such that rotated target feature 404fr is positioned at a position 406p within panoramic image view 406 relative to target feature 402fr in an accurate manner in the panoramic image view, with respect to rotation and distance, based on the motion data of the sensor 101s. In this way, template matching in frame_$t_1$ (i.e., digital image 404) may be performed by using a feature (e.g., target feature 402O of frame_t0 (e.g., digital image 402). $\delta_x$ and $\delta_y$ may be calculated by the coordinate difference: $\delta_x$=x$t_1$−x$t_0$; $\delta_y$=y$t_1$−y$t_0$. Thus, after correction of the second image via rotation and positioning with the motion data of the sensor (e.g., IMU sensor signal data), then stitching and reconstructing of the images may be performed to generate a panoramic image view as described herein. In addition, a total horizontal moving distance and a total vertical moving distance may be generated, which may be used to determine or generate a tracking trajectory for a plurality of images, which is further described herein for FIG. 7.

While FIG. 4 demonstrates image stitching between a first image (e.g., digital image 402, such as frame_$t_0$) and a second image (e.g., digital image 404, such as frame_$t_1$), it is to be understood that imaging stitching, as implemented by, and as described for, digital image stitching algorithm 400, may be performed for additional images of which first image (e.g., digital image 402, such as frame_$t_0$) and second image (e.g., digital image 404, such as frame_$t_1$) may only be a part. For example, a third image (not shown) may be image stitched with the second image (e.g., digital image 404) using template matching as described for digital image stitching algorithm 400. Still further, a fourth image (not shown) may be image stitched with the third image (not shown) using template matching as described for digital image stitching algorithm 400, and so forth and so on, where each of the images, as stitched together with digital image stitching algorithm 400 comprise or generate a panoramic image view, a horizontal and vertical moving distance, and/or a trajectory defining movement as described herein. In some aspects, a panoramic image view, horizontal and vertical moving distance values, and/or a trajectory value defining movement, may be saved or stored in computer memory such that the digital images remain separate, e.g., as separate images in memory, that overlapped according the angling (e.g., angle 404a), positioning information (e.g., position 406p), horizontal and vertical moving distance values, and/or a trajectory value defining movement, each of which may also be stored in computer memory. Additionally, or alternatively, a panoramic image view may be saved or stored in computer memory as a single entity (e.g., file) where the panoramic image view has been rasterized or vectored to as a single image having pixels representing the angling (e.g., angle 404a) and/or positioning information (e.g., position 406p) as previously determined for the one or more images used to generate the panoramic image view. In various aspects, panoramic image view(s) may be stored in a memory of computing device 111c1 and/or of server(s), such as database 105 and/or memory 106.

Figure 5:
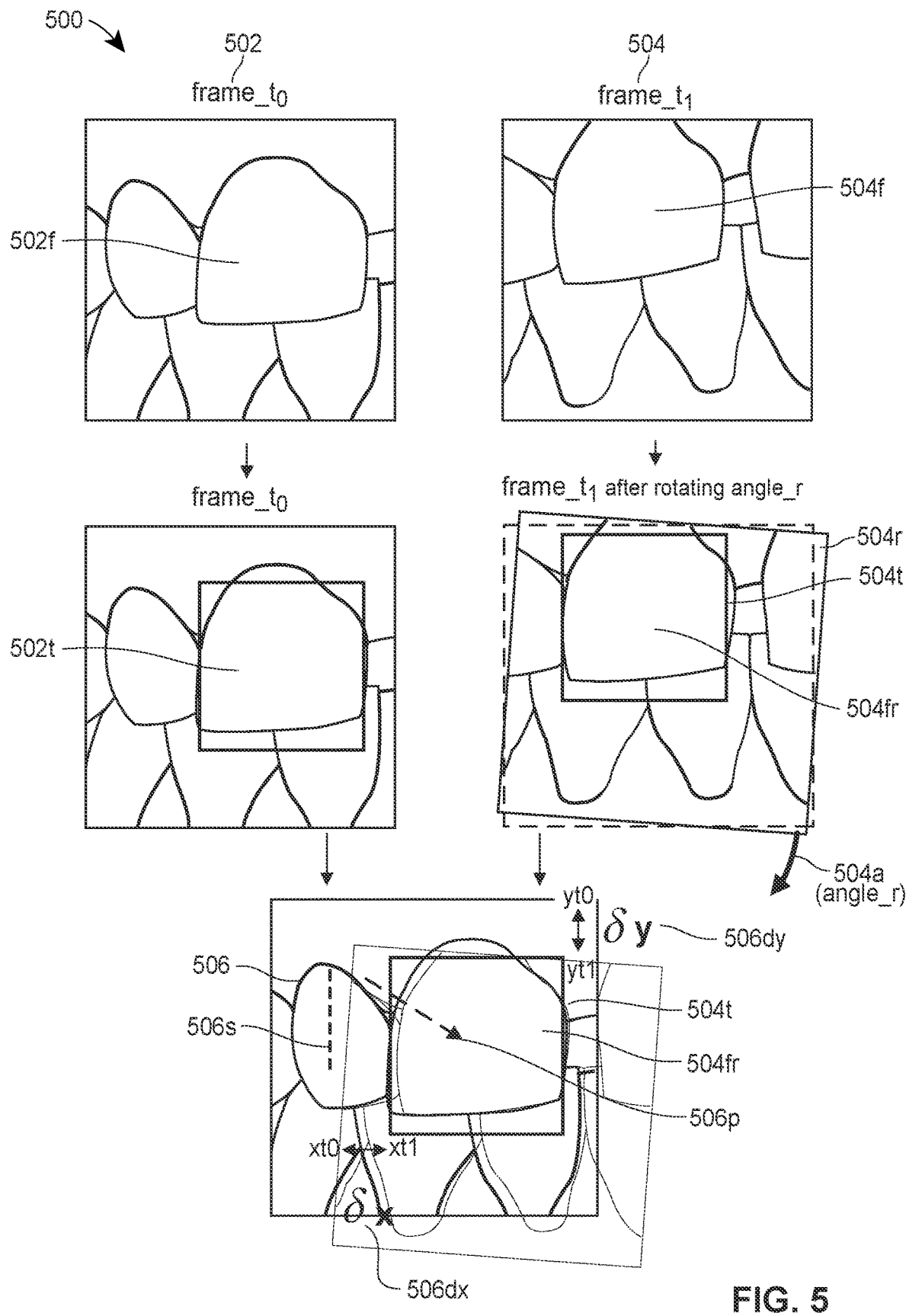
FIG. 5 illustrates an example of application of the digital image stitching algorithm of FIG. 4 as applied to an oral area, in accordance with various aspects disclosed herein.

FIG. 5 illustrates an example of application of the digital image stitching algorithm 400 of FIG. 4 as applied to an oral area, in accordance with various aspects disclosed herein. Accordingly, the disclosure for FIG. 4 applies in the same or similar manner for FIG. 5. In the example of FIG. 5, the application area may be, by way of non-limiting example, an oral application area (e.g., depicting a mouth, teeth, gums, or other oral features) and where the camera (e.g., camera 101c) is an intraoral camera that captures oral images of the oral application area. More generally, for an oral application area a digital image (e.g., digital image 502, i.e., frame_$t_0$, and digital image 504, i.e., frame_$t_1$) may depict one or more of one or more teeth, soft human tissue (e.g., gums, lounge, etc.), oral residue (e.g., plaque), or an artificial oral material (e.g., teeth filling, braces, retainer, artificial teeth, etc.). Each of the images (e.g., digital images 502 and 504) of FIG. 5 may comprise a plurality of pixels. The pixel data, and features thereof, may define the target feature (e.g., target feature 502f, e.g., a tooth) in the image.

More specifically, as shown for FIG. 5, a first area in the first image (e.g., digital image 502) is selected as a template 502t for the target feature 502f (i.e., a tooth). The location of template 502t can be determined or based on a center pixel of the digital image 502 itself and/or one or more pixels of the target feature 502f. An angle 504a can then be determined for a second image (e.g., digital image 504). For example, generating the angle 504a of the second image may comprise determining one or more angular velocity(s) of the sensor (e.g., sensor 101s). For example, this may comprise determining angular velocity change based on the motion data of the sensor as captured as the scanner device 101 moved relative to the object (e.g., a tooth as shown for FIG. 5) that comprises the target feature (e.g., 502f, which is the tooth as shown as pixel data in digital image 502, frame_t0) and as shown the first and second images (e.g., digital image 502 and digital image 504). A tilt angle 504a may then be determined for the second image based on the angular velocity change from the first image to the second image. The second image (e.g., digital image 504) may then be rotated (504r) by the tilt angle 504a, thus causing target feature 504f in digital image 504 (which corresponds to target feature 502O to likewise be rotated (e.g., rotated target feature 504fr) relative to the first image. Said another way, the angular velocity change at time to at coordinate ($x_0$, $y_0$) from the first image to the second image at time $t_1$ at coordinate ($x_1$, $y_1$) may be determined from the motion data. In some aspects, the angular velocity change may be used to generate a delta angle (e.g., tilt angle 504a). This delta angle (e.g., tilt angle 504a) may then be used for rotating the second image for orientation with respect to the first image. In this way, correction of the second image via rotation based on sensor data improves the precision of template matching for the oral application on a frame-by-frame basis.

Once rotated, digital image stitching algorithm 400 can generate a panoramic image view (e.g., panoramic image view 506) distance, and/or trajectory information of or corresponding to the oral application area from the first image and the second image (as rotated) by positioning the first image and the second image based on the sensor data. For example, generating a position of the second image 504 may comprise determining a first image feature (e.g., a central feature in for a template, e.g., template 502t, or otherwise pixel or group of pixels corresponding to an item depicted in the first image, such as target feature 502f, a tooth) within the first image (e.g., digital image 502), and determining a second image feature (e.g., rotated target feature 504fr, the same tooth) within the second image. The first image feature (e.g., target feature 502O may correspond to the second image feature (e.g., rotated target feature 504fr, the tooth), where a coordinate distance is determined between the first image feature (e.g., target feature 502f, the tooth) and the second image feature (e.g., rotated target feature 504fr, the tooth as rotated). The coordinate distance may then be used to set the position 506p of the second image as rotated by offsetting the second image from the first image by the coordinate distance. In the example of FIG. 5, the coordinate distance is comprised of a horizontal distance, i.e., $\delta_x$ (506dx) and a vertical distance, i.e., $\delta_y$ (506dy) such that second image as rotated (504r) is offset by the coordinate distance, formed by both the horizontal distance $506dx$ and vertical distance $506dy$, causing target feature $504fr$ of template $504t$ to be both positioned and offset from, and angled relative to, target feature $502f$ of template $502t$, such that rotated target feature $504fr$ is positioned at a position $506p$ within panoramic image view $406$ relative to target feature $502fr$ in an accurate manner in the panoramic image view, with respect to rotation and distance, based on the motion data of the sensor $101s$. In this way, template matching in frame_$t_1$ (i.e., digital image $504$) may be performed by using a feature (e.g., target feature $502f$) of frame_$t0$ (e.g., digital image $4502$). $\delta_x$ and $\delta_y$ are calculated by the coordinate difference: $\delta_x = xt_1 - xt_0$; $\delta_y = yt_1 - yt_0$. Thus, after correction of the second image via rotation and positioning with the motion data of the sensor (e.g., IMU sensor signal data), then stitching and reconstructing of the images may be performed to generate a panoramic image view as described herein. In the example of FIG. 5, image $504$ is shown as placed on top of image $502$, and is rotated correctly to allow the images to line up, overlap, or otherwise be positioned next to one another to accurately depict the oral application area, and related features (e.g., gums teeth) in the oral application area, as image stitched ($506s$) in the panoramic image view.

Figure 6A:
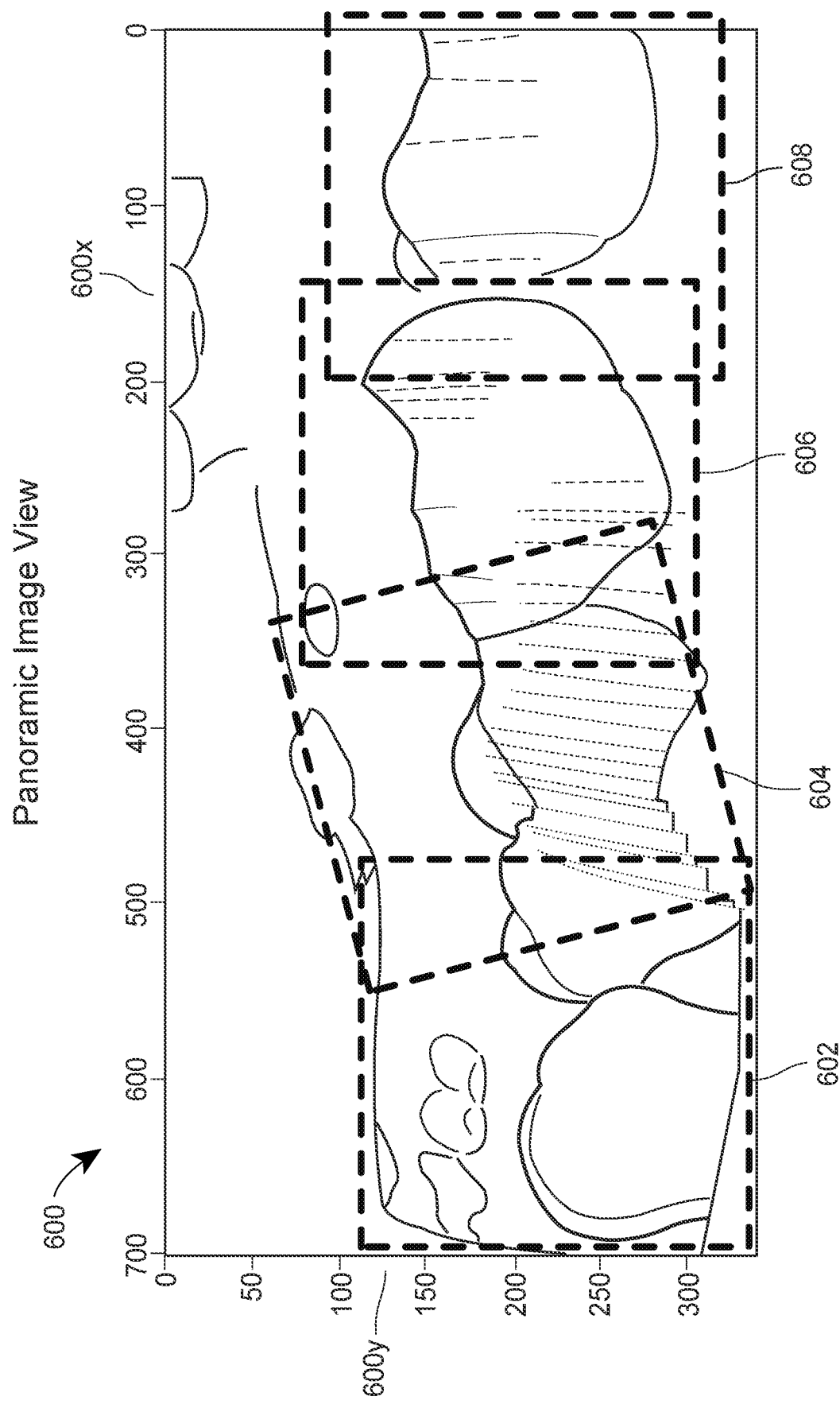
FIG. 6A illustrates an example panoramic image view, in accordance with various aspects disclosed herein.

FIG. 6A illustrates an example panoramic image view $600$, in accordance with various aspects disclosed herein. In the example of FIG. 6A, multiple digital images (e.g., digital images $602$-$608$), each comprising a pixel resolution of 224×224 pixels, have been stitched together (e.g., rotated and/or positioned) using, for example, the digital image stitching method $300$ of FIG. 3, which may comprise use of the digital image stitching algorithm $400$ as described for FIGS. 4 and 5 herein. The digital images, as used to generate panoramic image view $600$, may be been captured by an intraoral camera (e.g., camera $101c$) in an oral application area (e.g., a mouth of a user). As shown, panoramic image view $600$ depicts one or more target feature(s) (e.g., one or more teeth) in a wider field of view of the application area (e.g., oral application area) than any of the digital images $602$-$608$ alone.

As shown for FIG. 6A, vertical axis $600y$ is 300 pixels thereby fitting the 224×224 pixel images (e.g., digital images $602$-$608$) in the vertical dimension. Horizontal axis $600x$ is illustrated as 700 pixels and fits multiple, stitched 224×224 pixel images (e.g., digital images $602$-$608$) in the horizontal dimension. In some aspects, scan completion may be defined by maximum coordinate distance(s) of the image in the vertical and/or horizontal dimensions. Additionally, or alternatively, scan completion may be determined when a maximum number of images have been obtained by the camera (e.g., camera $101c$) and/or when such images have been stitched together. Scan completion may define when to generate a panoramic image view, such as panoramic image view $600$.

Figure 6B:
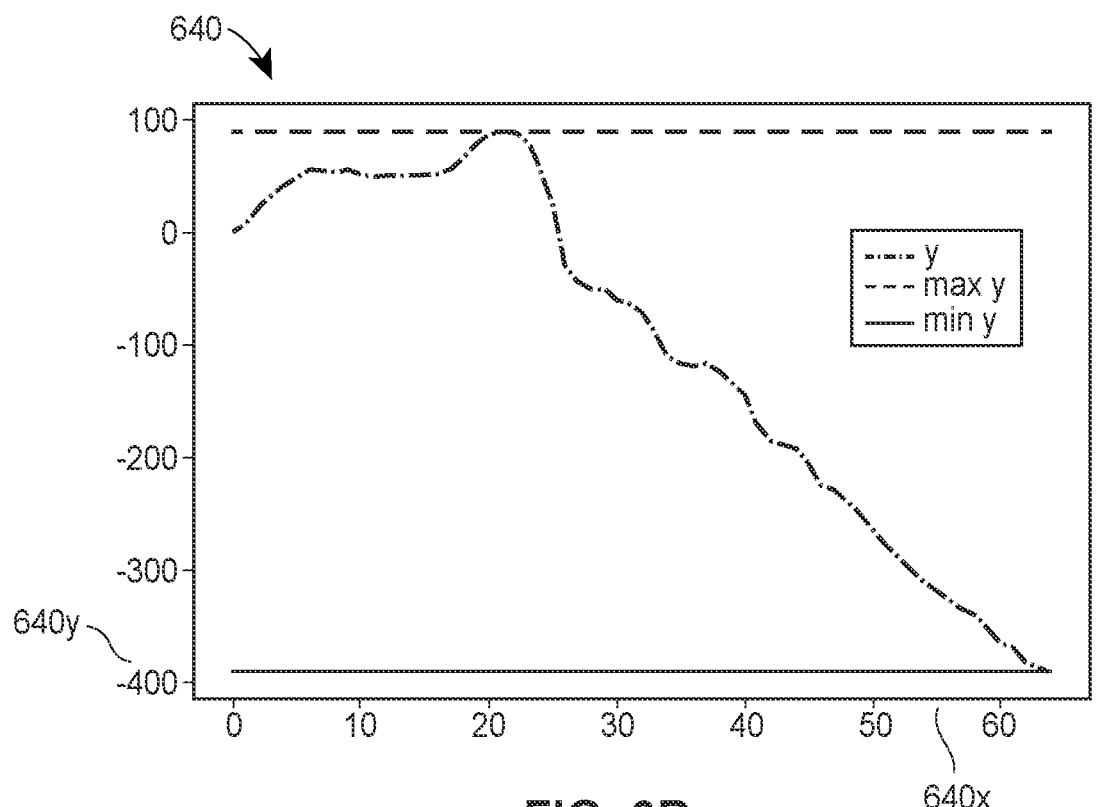
FIG. 6B illustrates a diagram showing vertical (y) offsets for positions of digital images used to generate the panoramic image view of FIG. 6A, in accordance with various aspects disclosed herein.

For example, FIG. 6B illustrates a diagram $640$ showing vertical (y) offsets for positions of digital images used to generate the panoramic image view of FIG. 6A, in accordance with various aspects disclosed herein. Specifically, axis $640y$ defines a cumulative offset amount or otherwise total distance coverage in the vertical dimension (y), which, in the example of FIG. 6B, is about 400 pixels of distance traversed (downward in the negative direction) among the digital images (e.g., digital images $602$-$608$) of panoramic image view $600$. Such cumulative offset amount or otherwise total distance may be a sum of $\delta_y$ values for the digital images (e.g., digital images $602$-$608$) of panoramic image view $600$. Axis $640x$ shows a number of digital images currently captured, for example, in the example FIG. 6B is about 60 digital images (all of which are not shown). Thus, diagram $640$ illustrates that cumulative vertical position traversed for a given number or count of images.

Figure 6C:
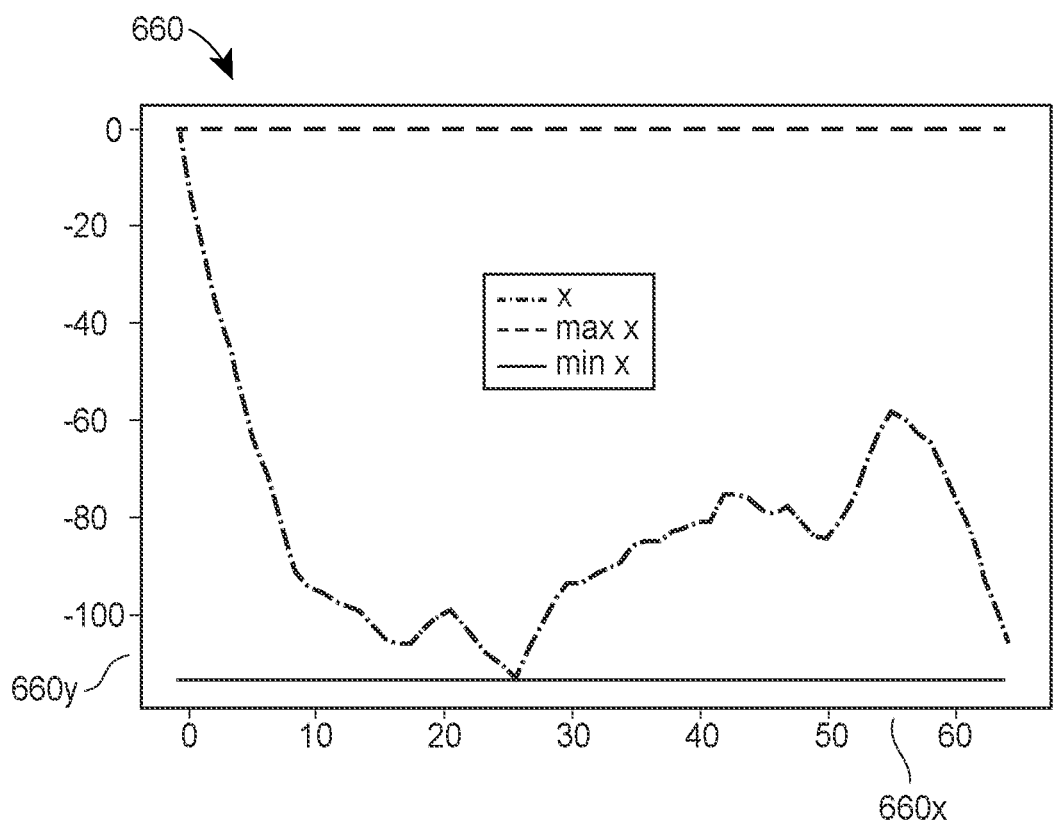
FIG. 6C illustrates a diagram showing horizontal (x) offsets for positions of digital images used to generate the panoramic image view of FIG. 6A, in accordance with various aspects disclosed herein.

Similarly, FIG. 6C illustrates a diagram $660$ showing horizontal (x) offsets for positions of digital images used to generate the panoramic image view of FIG. 6A, in accordance with various aspects disclosed herein. Specifically, axis $660y$ defines a cumulative offset amount or otherwise total distance coverage in the horizontal dimension (x), which, in the example of FIG. 6C, is about 100 pixels of distance traversed (sideways in the negative direction) among the digital images (e.g., digital images $602$-$608$) of panoramic image view $600$. Such cumulative offset amount or otherwise total distance may be a sum of $\delta_x$ values for the digital images (e.g., digital images $602$-$608$) of panoramic image view $600$. Axis $660x$ shows a number of digital images currently captured, for example, in the example FIG. 6C is about 60 digital images (all of which are not shown). Thus, diagram $660$ illustrates that cumulative horizontal position traversed for a given number or count of images.

In some aspects, panoramic image view $600$ may be generated following completion of determining that positioning of a plurality of images (e.g., digital images $602$-$608$) in the application area (e.g., an oral application area) equals or exceeds a maximum coordinate distance (e.g., such as 400 pixels in the vertical dimension and/or 100 pixels in the horizontal dimension as illustrated for FIGS. 6B and 6C). This may be implemented for example by a distance coverage algorithm: $\delta_{max\_x} > x_{threshold}$ and $\delta_{max\_y} > y_{threshold}$. The image distance coverage algorithm may comprise computing instructions implemented on one or more of the processors describe herein.

Additionally, or alternatively, panoramic image view $600$ may be generated following completion of determining that a threshold number of digital images of the plurality of images has been obtained (e.g., 60 images obtained for one or both of the vertical and/or horizontal dimensions as illustrated for FIGS. 6B and 6C). This may be implemented for example by an image count algorithm: e.g., valid frames or number of high-quality frames obtained$>N_{Threshold}$. The image count algorithm may comprise computing instructions implemented on one or more of the processors describe herein.

Figure 7:
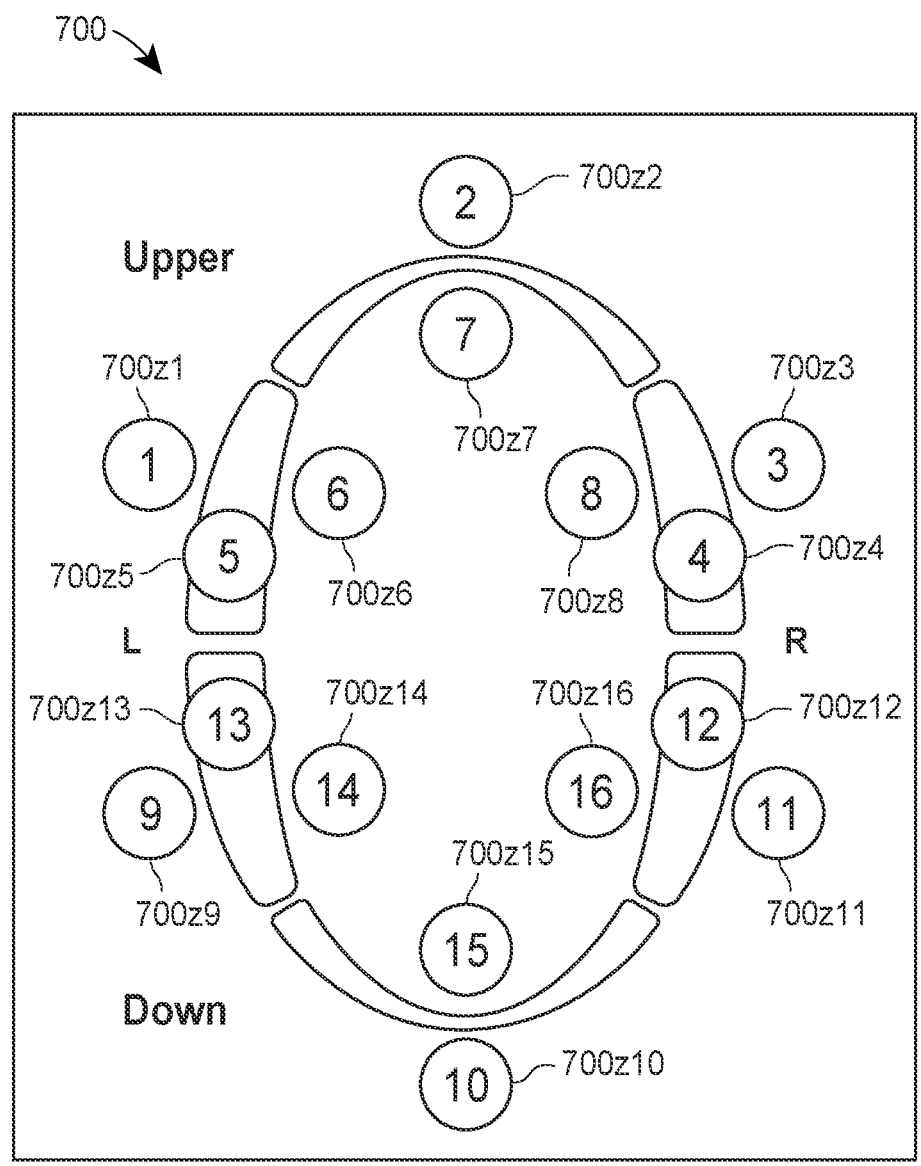
FIG. 7 illustrates zonal locations as predicted within an oral area, in accordance with various aspects disclosed herein.

FIG. 7 illustrates zonal locations (e.g., zonal locations $700z1$-$700z16$) as predicted within an oral area $700$, in accordance with various aspects disclosed herein. As shown for FIG. 7, oral area $700$ is an example of application area that comprises a representation of zones of a mouth having teeth at various zonal locations (e.g., zonal locations $700z1$-$700z16$). As shown, oral area $700$ comprises an upper area that represents the upper portion of a user's mouth. The inside of oral area represents the back of the user's teeth. The outside of the oral area represents the front of the user's teeth.

With reference to FIG. 7, the upper area of oral area $700$ includes outer upper zone location $700z2$ ("zone 2") and inner upper zone location $700z7$ ("zone 7"). The upper area of oral area $700$ further includes left side zones, including left side outer upper zone location $700z1$ ("zone 1"), left side inner upper zone location $700z6$ ("zone 6"), and left top side upper zone location $700z5$ ("zone 5," e.g., representing a top portion of the user's tooth, such as the top of a molar). Similarly, the upper area of oral area $700$ further includes right side zones, including right side outer upper zone location $700z3$ ("zone 3"), right side inner upper zone location $700z8$ ("zone 8"), and right top side upper zone location 700z4 ("zone 4," e.g., representing a top portion of the user's tooth, such as the top of a molar).

Further, with reference to FIG. 7, oral area 700 comprises a lower area (e.g., down area) that represents the bottom of a user's mouth. The lower area of oral area 700 includes outer lower zone location 700z10 ("zone 10") and inner lower zone location 700z15 ("zone 15"). The lower area of oral area 700 further includes left side zones, including left side outer lower zone location 700z9 ("zone 9"), left side inner lower zone location 700z14 ("zone 14"), and left top side lower zone location 700z13 ("zone 13," e.g., representing a top portion of the user's tooth, such as the top of a molar). Similarly, the upper area of oral area 700 further includes right side zones, including right side outer lower zone location 700z11 ("zone 11"), right side inner lower zone location 700z16 ("zone 16"), and right top side lower zone location 700z12 ("zone 12," e.g., representing a top portion of the user's tooth, such as the top of a molar).

In one aspect, digital image stitching (e.g., such as described herein for any one or more of FIGS. 3-5, or otherwise herein) may further comprise predicting or otherwise identifying zonal locations within oral area 700 based on one or more of a panoramic image view (e.g., panoramic image view 600) and/or the panoramic image view and the position data (e.g., relative position data as determined based on motion data of a sensor, such as an IMU sensor data, as described herein). In such aspects, the stitched results (e.g., panoramic image view position data, total horizontal and vertical distance value, and/or trajectory values) can be used to enhance zonal prediction accuracy and also enhance the certainty on determining whether or not a given zonal area (i.e., zone) has been scanned completely. For example, for some zones in an oral area, especially in zones with similar IMU data output, or located in symmetric locations within a user mouth, errors in identifying zones can occur where one zone that is similar to another is improperly identified. For example, when user scans zone 1, identification may incorrectly identify zone 16, which will affect the total precision, as well as the scan time needed for scanning and identifying these zones. However, by using information or data from the panoramic image view (e.g., panoramic image view 600) and/or the position data (e.g., relative position data), the zones may be more accurately predicted and thus identified. In one aspect, using information for zone identification or zone prediction, such as the distance moved in the x and y positions, i.e., $\delta_x$ and $\delta_y$, as two additional parameters, zonal prediction can be performed in a more accurate manner. For example, when $\delta_x$ and/or $\delta_y$ are too small to jump into another zone (e.g., the distance from zone 16 to zone 1 is too small based on the distance between one or more of $\delta_x$ and/or $\delta_y$ and the known or actual distance from zone 16 to zone 1), the prediction or identification of a zone result can be more accurately predicted. For example, for an incorrect prediction of zone 16, the prediction can be ignored or corrected from zone 16 back to the correct zone 1, therefore improving total accuracy of zonal prediction.

In some aspects, a positive indication is determined as part of the digital image stitching algorithm (e.g., such as described herein for any one or more of FIGS. 3-5, or otherwise herein). The positive indication can be based on the zonal locations and used to increase the accuracy of image matching in general. For example, in such aspects oral area 700 may comprise one or more zonal locations (e.g., zonal locations 700z1-700z16) including at least a first zonal location (e.g., zonal location 700z1) and a second zonal location (e.g., zonal location 700z2), and wherein the image matching of the second image with the first image (e.g., via image matching as describe herein) is further based on a positive indication that each of the second image and the first image are within the first zonal location. That is, the positive indication may improve the accuracy of image mapping by determining that each of the first and second image correctly belong to the first zonal location (e.g., zonal location 700z1).

Additionally, or alternatively, the positive indication may improve ignoring or forgoing images of zones that are outside of a given zone. For example, in some aspects, the plurality of digital images as captured by the camera further comprise a third image. In such aspects, the digital image stitching method or algorithm (e.g., such as described herein for any one or more of FIGS. 3-5, or otherwise herein) may further comprise determining that the third image depicts the second zonal location. Given that the third image belongs to the second zonal location (and not the first location), the digital image stitching method or algorithm forgoes or ignores image matching of the third image with either of the second image or the first image. That is, the image stitching algorithm forgoes or ignores image stitching based on the third image being in located the second zonal location, where the second zonal location is different from the first zonal location. Said another way, the third image is not stitched based on analysis of the zonal information (e.g., the user moved the scanner device from one zone to a different zone).

Although FIG. 7 depicts an oral area and describes zonal locations (zones) in terms of areas or locations of a mouth, it is to be understood that zonal locations may define zones, generally, within additional or different application areas, including those as described herein. In various aspects, the digital image stitching systems and methods as described herein can generate the panoramic image views in addition to generating a total distance moved in horizontal and vertical direction. In some aspects, such data can then be used to describe a completion of a scanning of one or more zones (e.g., default zones of a given application area). In addition, the image stitching systems and methods as described herein can also be used to generate a trajectory as determined from the plurality of images based on $\delta_x$ and $\delta_y$.

In such aspects, the digital image stitching systems and methods as described herein may comprise determining one or more zonal locations within the application area. The digital image stitching systems and methods may further comprise generating, based on the image matching of the second image (e.g., digital image 404) with the first image (e.g., digital image 402) based on the angle or the position of the second image, a distance moved in a horizontal direction and in a vertical direction. The distance moved may define a movement of the camera (e.g., camera 101c) from a first position when the first image was captured to a second position when the second image was captured. The digital image stitching systems and methods may further comprise generating, based on the distance moved in the horizontal direction and the vertical direction, a total distance defining a total movement. The digital image stitching systems and methods may further comprise determining, based on the total movement, at least one of (i) a coverage amount occurring within at least one of the one or more zonal locations, or (ii) a trajectory value defining a trajectory within at least one of the one or more zonal locations. The digital image stitching systems and methods may further comprise generating an indication of whether a successful scan occurred based on at least one of the coverage amount or the trajectory value. In some aspects, the indication may be displayed or rendered on a GUI as a graphic, such as a GUI as described herein for FIG. 12.

In additional aspects, a total distance defining a total movement of the scanner device (e.g., scanner device 101) or portion thereof (e.g., camera 101c) may be determined. In such aspects, a digital image stitching method is implemented by capturing, by a camera (e.g., camera 101c) of a scanner device (e.g., sensor 101s), a plurality of digital images depicting a target feature within an application area. The plurality of digital images may comprise at least a first image (e.g., digital image 402) and a second image (e.g., digital image 404). The digital image stitching method may further comprise capturing, by a sensor (e.g., sensor 101s) coupled to the scanner device (e.g., scanner device 101), motion data as the scanner device moves relative to the target feature. The digital image stitching method may further comprise determining relative position data based on the motion data, the relative position data comprising at least first position data corresponding to the first image and second position data corresponding to the second image. The digital image stitching method may further comprise generating, based on the relative position data, at least one of an angle or a position of the second image relative to the first image. The digital image stitching method may further comprise generating, based on image matching of the first image with the second image and one or more distances moved in respective horizontal and vertical directions, a total distance defining a total movement. The total distance may comprise a total sum of the delta values in the y-axis (vertical) and x-axis (horizontal) positions among one or more of the images captured (e.g., the first image and the second image). In this way, delta values (i.e., $\delta_x$ and $\delta_y$) may be calculated by the respective coordinate differences (i.e., $\delta_x = xt_1 - xt_0$; $\delta_y = yt_1 - yt_0$) and summed in order to determine the total distance defining the total movement of the sensor 101s. In some aspects, the digital imaging stitching method may comprise generating a panoramic image view (e.g., panoramic image view 406) depicting the target feature in a wider field of view of the application area than either the first image or the second image.

In additional aspects, a digital imaging method for determining a successful scan completion of a scan of a zone (e.g., one of zonal locations 700z1-700z16) is disclosed. In such aspects, the digital imaging method comprises capturing, by a camera (e.g., camera 101c) of a scanner device (e.g., scanner device 101), a plurality of digital images depicting a target feature within an application area. The plurality of digital images may comprise at least a first image (e.g., digital image 404) and a second image (e.g., digital image 406). The digital imaging method may further comprise capturing, by a sensor (e.g., sensor 101s) coupled to the scanner device, motion data as the scanner device moves relative to the target feature. The digital imaging method may further comprise determining relative position data based on the motion data. The relative position data may comprise at least first position data corresponding to the first image and second position data corresponding to the second image. The digital imaging method may further comprise generating, based on the relative position data, at least one of an angle or a position of the second image relative to the first image. The digital imaging method may further comprise generating, based on image matching of the second image with the first image based on the angle or the position of the second image, a distance moved in a horizontal direction or a distance moved in a vertical direction. Such horizontal direction and vertical direction may be determined by one or more delta values (i.e., $\delta_x$ and $\delta_y$) as calculated based on respective coordinate differences (i.e., $\delta_x = xt_1 - xt_0$; $\delta_y = yt_1 - yt_0$) of the captured images. The distance may define movement of the camera when capturing the images, e.g., the first image and the second image. The digital imaging method may further comprise determining a zone scan completion (i.e., the completion of scanning a zone) based on the distance moved in the horizontal direction or the distance moved in the vertical direction. The zone scan completion may define a total distance of a total movement of the scan with respect to at least one preset threshold value. The preset threshold value may be defined in terms of quantity, where quantity relates to a quantity or number of images captured and scanned for a given zone. For example, the digital imaging method may further comprise determining the zone scan completion further based on a required amount of the plurality of images collected (e.g., quantity) within the zone with respect to at least one preset threshold number defining the completion of one or more zones. An example of quantity may be 115% meaning that 115% of the threshold number of images need to be detected in order to achieve successful scan completion of a zone. Additionally, or alternatively, the zone scan completion may be determined in terms of coverage, where coverage defines a number of pixels within the zone defining movement. An example of coverage may be 125% meaning that 125% of movement, as determined from a number of pixels traversed, or otherwise detected or scanned within the zone, needs to be detected in order to achieve successful scan completion of a zone (e.g., one of zonal locations 700z1-700z16). In some aspects, a zone scan completion may be determined based on a combined quantity and coverage preset threshold values where the combined value may be, for example a value of "1", where the zone scan completion is achieved when the preset threshold value is equal to or greater than 1 (e.g., 100%). The preset threshold value (e.g. for coverage) and/or the preset threshold number (e.g., for quantity) may be predetermined or preset prior to beginning the scan with the scanner device 101. These values maybe updated, changed, or otherwise modified in order to adjust zone scan completion behavior.

Figure 8:
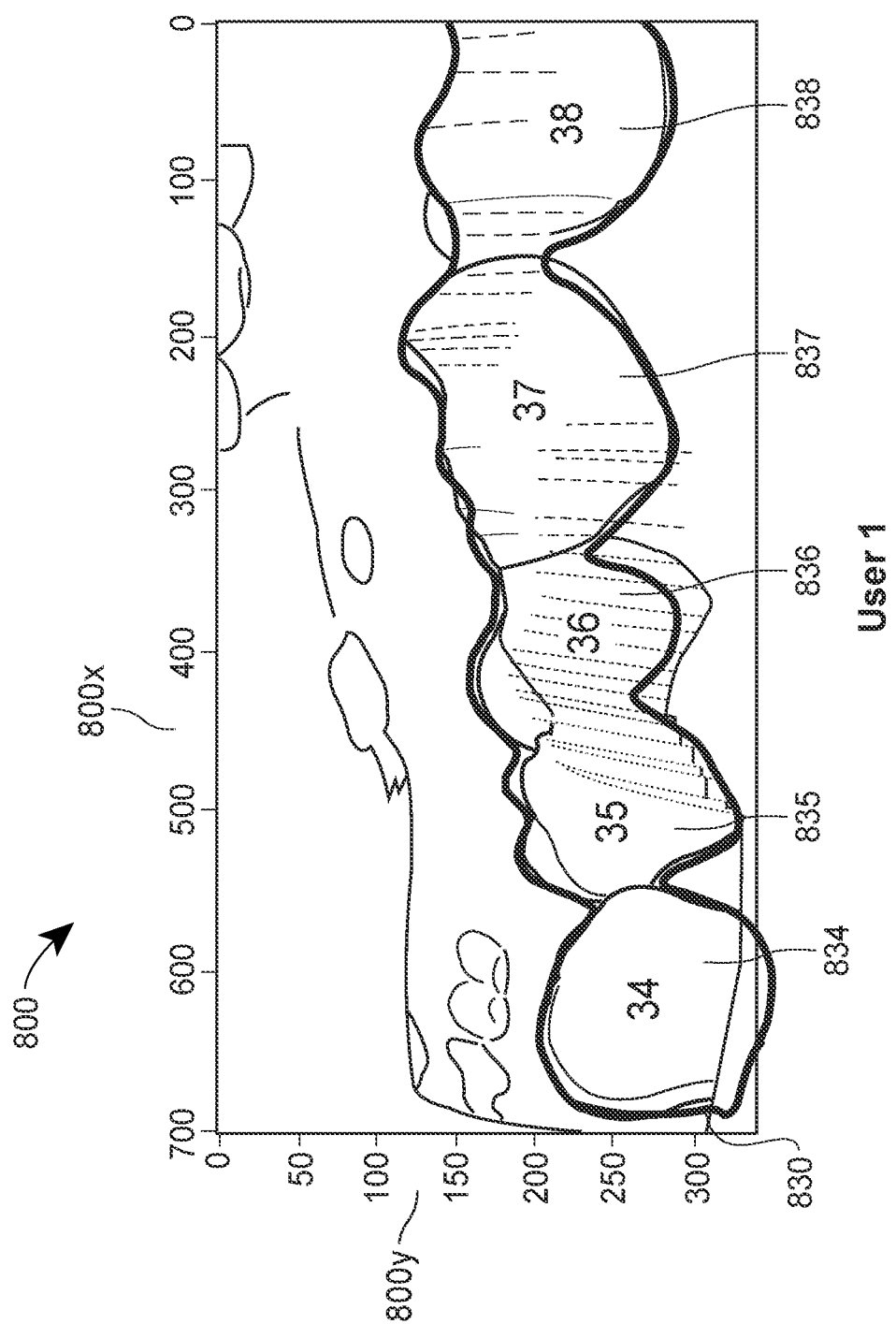
FIG. 8 illustrates an example a tooth position of one or more teeth within an oral area, in accordance with various aspects disclosed herein.

FIG. 8 illustrates an example one or more tooth positions of one or more teeth within an oral area, in accordance with various aspects disclosed herein. As shown for FIG. 8, an example panoramic image view 800 is shown. Panoramic image view 800 may the same or similar to that of panoramic image view 600 as described herein for FIG. 6A, such that the disclosure of FIG. 6A applies the same or similar with respect to panoramic image view 800. For example, multiple digital images (e.g., digital images 602-608), each comprising a pixel resolution of 224×224 pixels, may have been stitched together (e.g., rotated and/or positioned) using, for example, the digital image stitching method 300 of FIG. 3, which may comprise use of the digital image stitching algorithm 400 as described for FIGS. 4 and 5 herein. The digital images, as used to generate panoramic image view 600, may be been captured by an intraoral camera (e.g., camera 101c) in an oral application area (e.g., a mouth of a user). As shown, panoramic image view 800 depicts one or more target feature(s) (e.g., one or more teeth) in a wider field of view of the application area (e.g., oral application area) than any of the digital images alone (e.g., digital images 602-608) as may have been used to generate panoramic image view 800.

As shown for FIG. 8, vertical axis 800y is 300 pixels thereby fitting the 224×224 pixel digital images (e.g., such as digital images 602-608) in the vertical dimension. Horizontal axis 800x is illustrated as 700 pixels and fits multiple, stitched 224×224 pixel images (e.g., digital images 602-608) in the horizontal dimension. As shown for FIG. 8, positions of features of panoramic image view 800 (e.g., such as positions of one or more teeth) may be determined or predicted. As shown for FIG. 8, panoramic image view 800 includes positions for various teeth in the oral area of a user's mouth, including tooth position 834, tooth position 835, tooth position 836, tooth position 837, and tooth position 838. Each of the teeth, and their various positions may be determined or predicted by the digital imaging stitching method to provide a tooth level position or prediction. For example, in some aspects, the digital image stitching method or algorithm (e.g., the digital image stitching method 300 of FIG. 3, which may comprise use of the digital image stitching algorithm 400 as described for FIGS. 4 and 5 herein) may further comprise predicting a tooth position (e.g., any one or more of tooth position 834-838) of one or more teeth depicted within the oral area, e.g., panoramic image view 800. In some aspects, the panoramic image view 800 may be generated following completion of determining that a minimum number of teeth (e.g., at least teeth at positions 834-838) have been scanned in the oral area. In this way, a minimum of teeth for a given zonal area can be used to indicate scan completion, so that the scan accuracy for the panoramic image view is improved based on tooth level precision.

The prediction may be based on one or more of the panoramic image view 800 alone or the panoramic image view 800 and the position data (e.g., position data as determined from motion/sensor data). More specifically, by calculating distances of respective tooth positions (e.g., $\delta_x$ and/or $\delta_y$), a series of images of teeth can be overlaid together to form a 2D panoramic image view, e.g., panoramic image view 800, as described herein for FIGS. 6A-6C. With tooth level prediction, accuracy of the 2D panoramic image view can be improved by analyzing the tooth position in every zone and post processing the panoramic image 2D panoramic image view, e.g., panoramic image view 800, where the teeth included in a given zone can be outlined (830) and marked as shown in FIG. 8. The various images that comprise the panoramic image view 800 can be adjusted to fit the outline thereby increasing the position prediction precision at the tooth level, and therefore the accuracy of the panoramic image view (e.g., panoramic image view 800) as a whole.

Figure 9:
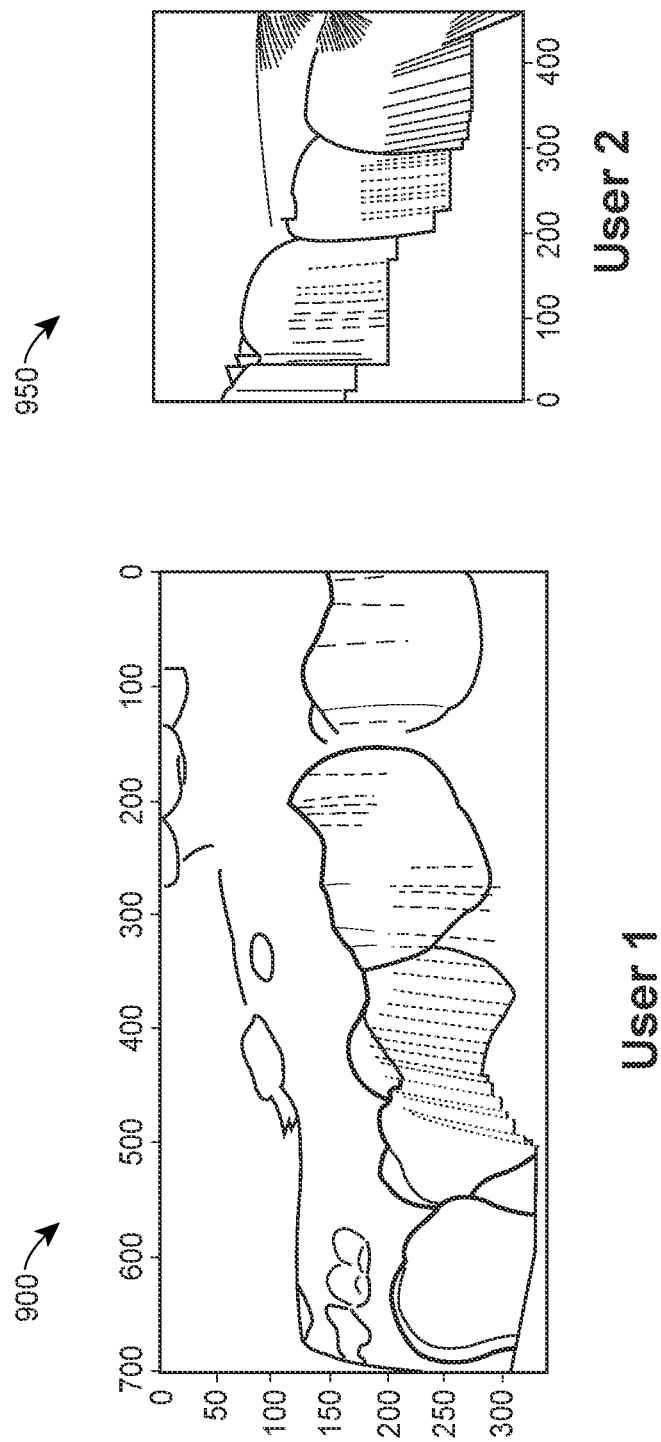
FIG. 9 illustrates example panoramic image views of respective oral areas of a first user and a second user where each panoramic image view has one or more unique oral features corresponding the respective user.

FIG. 9 illustrates example panoramic image views (e.g., panoramic image view 900 and panoramic image view 950) of respective oral areas of a first user (e.g., user 1) and a second user (e.g., user 2) where each panoramic image view has one or more unique oral features corresponding the respective user. Each of panoramic image view 900 and panoramic image view 950 may have been generated using, for example, the digital image stitching method 300 of FIG. 3, which may comprise use of the digital image stitching algorithm 400 as described for FIGS. 4 and 5, or as described for any one or more FIGS. 6A-6C, 8 and/or as otherwise herein.

Panoramic image view 900 and panoramic image view 950 represent different images for each of the respective users, and thus each of panoramic image view 900 and panoramic image view 950 illustrate personal identification (or finger printing) by using panoramic image views, e.g., images of teeth in the example of FIG. 9. Thus, in some aspects, a digital image stitching method may further comprise identifying a user based on one or more unique oral features of the user depicted by the panoramic image view. The images can be used as a template to match to a given person. In some aspects, the each user may have a personal ID. For example, when multiple users exist, this aspect of the digital stitching method can reconstruct image to a 2D model, or additionally or alternatively a 3D model (e.g., based on the stitching result and information from the sensors), for use of identifying which user is using the scanner device. Based on the user, the scanner device may be differently configured or otherwise use different settings to accommodate the user's needs and/or preferences for use of the scanner device.

Figure 10:
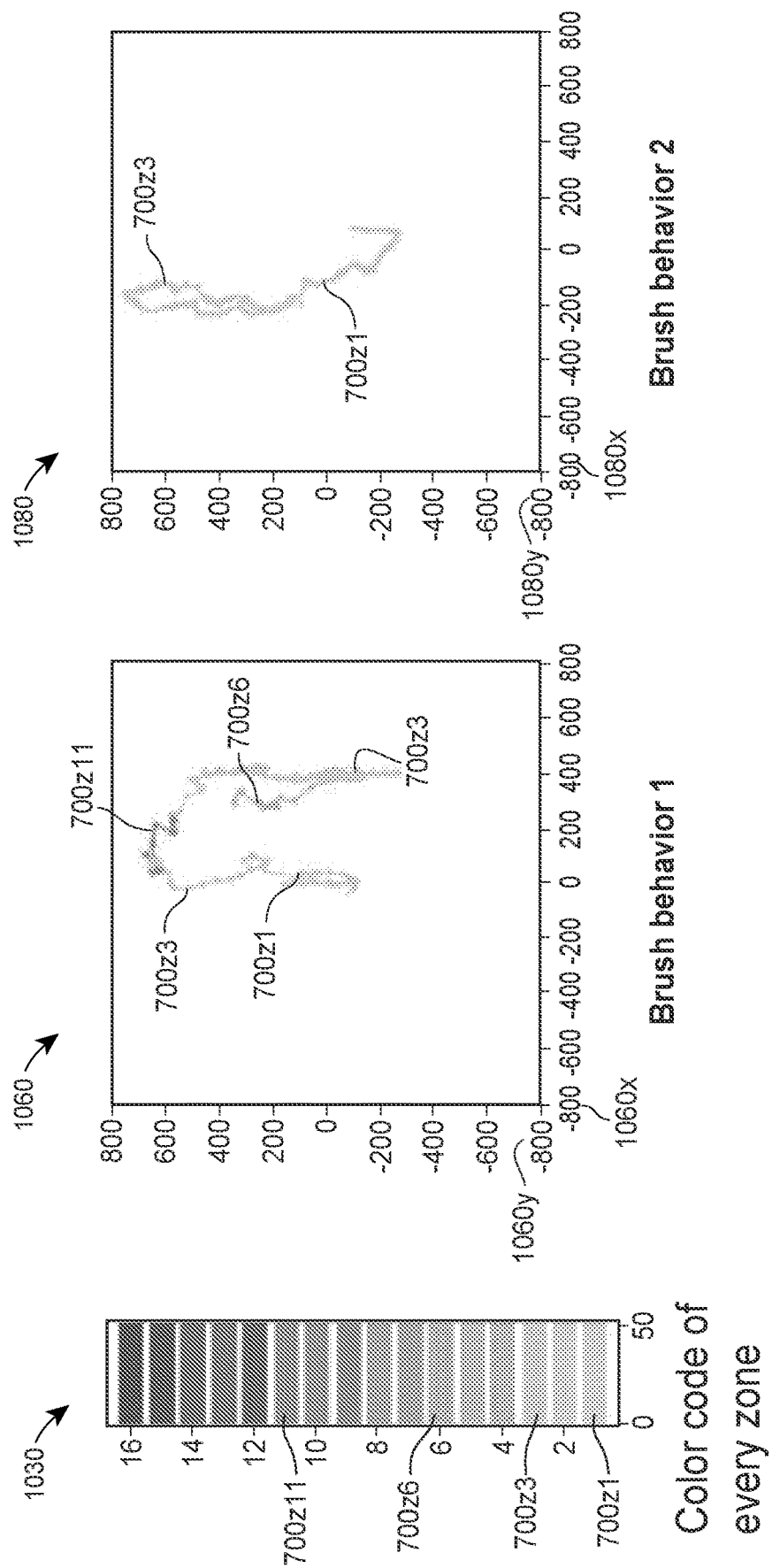
FIG. 10 illustrates an example diagrams indicating unique scan behaviors of respective users, in accordance with various aspects disclosed herein.

FIG. 10 illustrates an example diagrams indicating unique scan behaviors (e.g., scan behaviors of scan behavior diagrams 1060 and 1080) of respective users, in accordance with various aspects disclosed herein. In the example of FIG. 10, scan behaviors of scan behavior diagrams 1060 and 1080 comprise brush behaviors (e.g., as determined by respective scans by scanner device 101) of a first user and a second user (e.g., which may correspond to user 1 and user 2, respectively, as described for FIG. 9). The brush behaviors may comprise unique brushing behaviors of the first user and the second user. In this way, such brush behavior may be used to uniquely identify users based on patterns identifiable within the scan data. More generally, the digital image stitching method or algorithm as described herein (e.g., the digital image stitching method 300 of FIG. 3, which may comprise use of the digital image stitching algorithm 400 as described for FIGS. 4 and 5 herein) may further comprise identifying one or more users (e.g., user 1 and user 2) based on one or more unique scan behaviors of the position data (e.g., as determined from scan data of scanner device 101), thereby providing personal identification based on user scan behavior.

Each user typically exhibits a unique brush behavior that can be reconstruct to identify the user and server as a type of oral "fingerprint." It is to be noted, however, that a given user's brush behavior (or more generally scan behavior for non-oral aspects) is nonetheless highly abstracted, and does not necessarily give away personal identifiable information (PII) of a user. Thus, scanner behavior identification (e.g., brush behavior) can have the dual benefit of user identification but without revealing or comprising PII.

As shown in the example FIG. 10, zonal locations (e.g., zonal locations 700z1-700z16, corresponding to zone 1 to zone 16) of oral area 700 are illustrated for reference. Each of the zonal locations (e.g., zonal locations 700z1-700z16) correspond to a color code as shown for color code diagram 1030, where a different color (or pattern) is shown for each of the zonal locations (e.g., zonal locations 700z1-700z16). For example, a first color or pattern (e.g., pink) may be shown for zonal location 700z1 (zone1), a third color or pattern (e.g., orange) may be shown for zonal location 700z3 (zone3), a sixth color or pattern (e.g., blue) may be shown for zonal location 700z6 (zone6), and an eleventh color or pattern (e.g., red) may be shown for zonal location 700z10 (zone10). There may be 16 total color or patterns that correspond to the 16 zonal locations. It is to be understood, however, that greater or fewer colors can be used and/or greater zonal locations. In addition, it is to be understood that colors may be blended or mixed such that a color in between two zonal locations may be a mix or blend of colors of those two zonal locations.

Scan behavior diagram 1060 comprises a y-axis 1060y indicating brush movement (e.g., as determined by $\delta_y$ as described herein) of a first user (e.g., user 1). Further, behavior diagram 1060 comprises an x-axis 1060x indicating brush movement (e.g., as determined by $\delta_x$ as described herein) of the first user (e.g., user 1). Each of y-axis 1060y and x-axis 1060x are measured across ranges of −800 to 800, which may present a real distance (e.g., millimeters) or pixels moved (e.g., pixels moved within a given a panoramic image view or otherwise set of digital images as described herein). The first user's scan behavior (e.g., brush behavior) can then be determined based not only on distance moved, but also zonal locations the scanner device traveled to, during use of the scanner device (e.g., use of oral scanner, toothbrush, etc.). For example, as shown for scan behavior diagram 1060, the first user moved the oral scanner (e.g., scanner device 101) within his or her oral area (e.g., mouth) in a y-axis direction of about −200 to 600 and in an x-axis direction of about 0 to 400, and through zonal locations 700z1 (zone 1), 700z3 (zone 3), 700z6 (zone 6), and 700z11 (zone 11). In this way, the first user (e.g., user 1), has a unique behavior with respect to operating or otherwise using the scanner device within his or her oral area.

Similarly, scan behavior diagram 1080 comprises a y-axis 1080y indicating movement (e.g., as determined by $\delta_y$ as described herein) of a second user (e.g., user 2). Further, behavior diagram 1080 comprises an x-axis 1080x indicating brush movement (e.g., as determined by $\delta_x$ as described herein) of the second user (e.g., user 2). Each of y-axis 1080y and x-axis 1080x are measured across ranges of −800 to 800, which may present a real distance (e.g., millimeters) or pixels moved (e.g., pixels moved within a given a panoramic image view or otherwise set of digital images as described herein). The second user's scan behavior (e.g., brush behavior) can then be determined based not only on distance moved, but also zonal locations the scanner device traveled to, during use of the scanner device (e.g., use of oral scanner, toothbrush, etc.). For example, as shown for scan behavior diagram 1080, the second user moved the oral scanner (e.g., scanner device 101) within his or her oral area (e.g., mouth) in a y-axis direction of about −200 to 800 and in an x-axis direction of about −200 to 100, and through zonal locations 700z1 (zone 1) and 700z3 (zone 3). In this way, the first user (e.g., user 1), has a unique behavior with respect to operating or otherwise using the scanner device within his or her oral area.

In some aspects, the scan data may be collected for a given period of time (e.g., 15 seconds) such that the scan behaviors of some users may be more complete than others, where some users (e.g., user 2) may take longer to move the scanner device (e.g., oral device, such as taking longer to brush teeth) as compared to other users (e.g., user 1). This is represented in the example scan behavior diagrams 1060 and 1080 of FIG. 10.

Figure 11:
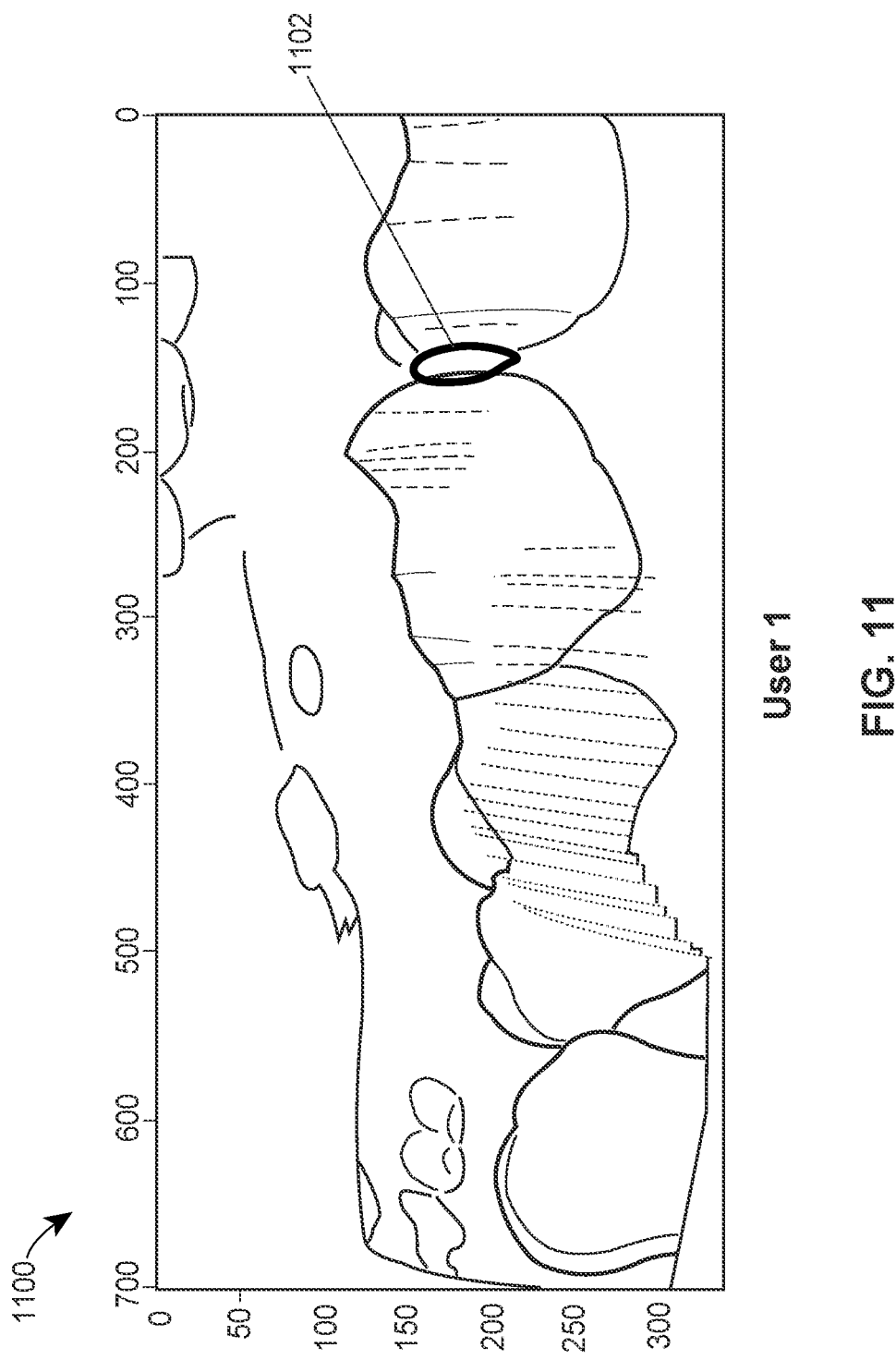
FIG. 11 illustrates an example panoramic image view comprising an indication of a tooth contaminant on one or more teeth depicted within the panoramic image view, in accordance with various aspects disclosed herein.

FIG. 11 illustrates an example panoramic image view 1100 comprising an indication of a tooth contaminant 1102 on one or more teeth depicted within the panoramic image view 1100, in accordance with various aspects disclosed herein. Panoramic image view 1100 may the same or similar to that of panoramic image view 1100 as described herein for FIG. 6A, such that the disclosure of FIG. 6A applies the same or similar with respect to panoramic image view 1100. For example, multiple digital images (e.g., digital images 602-608), each comprising a pixel resolution of 224×224 pixels, may have been stitched together (e.g., rotated and/or positioned) using, for example, the digital image stitching method 300 of FIG. 3, which may comprise use of the digital image stitching algorithm 400 as described for FIGS. 4 and 5 herein. The digital images, as used to generate panoramic image view 1100, may be been captured by an intraoral camera (e.g., camera 101c) in an oral application area (e.g., a mouth of a user). As shown, panoramic image view 1100 depicts one or more target feature(s) (e.g., one or more teeth) in a wider field of view of the application area (e.g., oral application area) than any of the digital images alone (e.g., digital images 602-608) as may have been used to generate panoramic image view 1100.

As shown for FIG. 11, the application area is an oral area where tooth contaminant 1102 appears between two teeth depicted in panoramic image view 1100. In some aspects, the digital image stitching method or algorithm (e.g., the digital image stitching method 300 of FIG. 3, which may comprise use of the digital image stitching algorithm 400 as described for FIGS. 4 and 5 herein) may further comprise identifying an indication of a tooth contaminant on one or more teeth depicted within the panoramic image view. The tooth contaminant may comprise plaque, calculus, tartar, or other tooth contaminants or tooth wear or damage. The tooth contaminant(s) may be depicted in the panoramic image view 1100, and is determinable, for example, by the pixel data therein. In some aspects, tooth contaminant identification can be implemented at the frame level, where tooth contaminant may be identified in one or more image frames before the panoramic image view is generated or otherwise before image stitching is performed. Additionally, or alternatively, tooth contaminant may be identified after the panoramic image view is generated or otherwise after image stitching is performed.

In some aspects, multiple digital images, including one or more panoramic image view(s), may be used to track changes or evolution of the tooth contaminant over time. This can include tracking changes or evolution of tooth containment at one or more zone level(s) over time. For example, in some aspects, digital image stitching method or algorithm (e.g., the digital image stitching method 300 of FIG. 3, which may comprise use of the digital image stitching algorithm 400 as described for FIGS. 4 and 5 herein) comprises generating a second panoramic image view (e.g., a second version of panoramic image view 1100, not shown) at a second time (e.g., a second date, time, or otherwise in the future). In such aspects, the digital image stitching method or algorithm can further comprise identifying a second indication of a tooth contaminant (e.g., tooth contaminant 1102) on one or more teeth depicted within the second panoramic image view. The digital image stitching method or algorithm can further comprise determining a tooth contaminant evolution (e.g., a change, such as decrease, increase, or otherwise deviation in an amount of tooth contaminant) between the second indication of the tooth contaminant and the first indication of the tooth contaminant.

Figure 12:
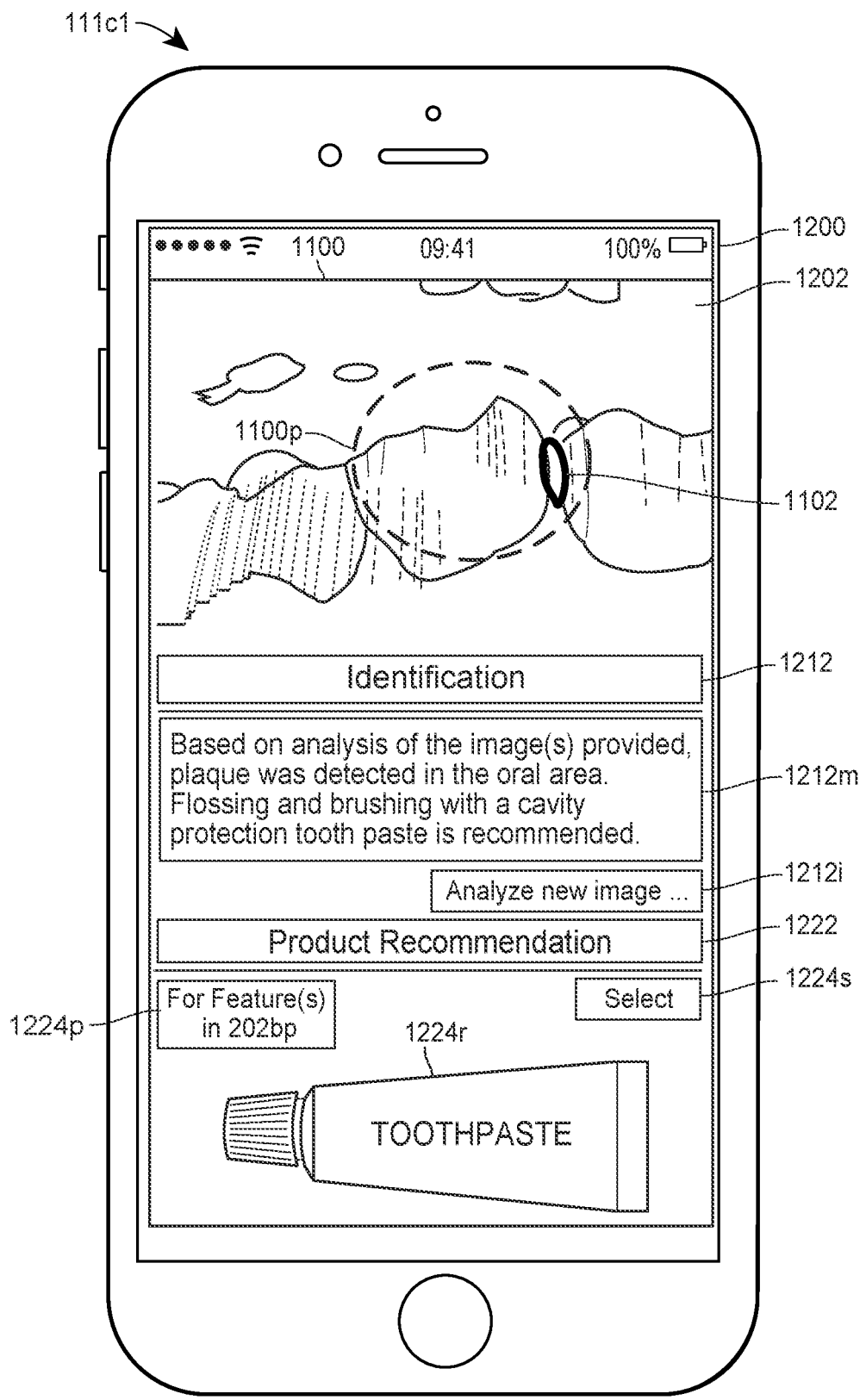
FIG. 12 illustrates an example user interface as rendered on a display screen of a user computing device in accordance with various aspects disclosed herein.

FIG. 12 illustrates an example user interface as rendered on a display screen 1200 of a user computing device (e.g., user computing device 111c1) in accordance with various aspects disclosed herein. For example, as shown in the example of FIG. 12, user interface 1202 may be implemented or rendered via an application (app executing on user computing device 111c1). For example, as shown in the example of FIG. 12, user interface 1202 may be implemented or rendered via a native app executing on user computing device 111c1. In the example of FIG. 12, user computing device 111c1 is a user computer device as described for FIG. 1 or FIG. 2, e.g., where 111c1 is illustrated as an APPLE iPhone that implements the APPLE iOS operating system and that has display screen 1200. User computing device 111c1 may execute one or more native applications (apps) on its operating system, including, for example, a mobile app (e.g., panoramic imaging app 108) as described herein. Such native apps may be implemented or coded (e.g., as computing instructions) in a computing language (e.g., SWIFT) executable by the user computing device operating system (e.g., APPLE iOS) by the processor of user computing device 111c1. In various aspects, the imaging app (e.g., a panoramic imaging app 108) executing on a mobile device, such as user computing device 111c1, may be referred to as a panoramic imaging app, designed to capture digital images and sensor data and generate a panoramic image view as described herein.

Additionally, or alternatively, user interface 1202 may be implemented or rendered via a web interface, such as via a web browser application, e.g., Safari and/or Google Chrome app(s), or other such web browser or the like.

In various aspects, a panoramic image view may be rendered via a graphic user interface (GUI) on a display screen (e.g., display screen 1200). As shown in the example of FIG. 12, a panoramic image view (e.g., panoramic image view 1100) may be, with graphical annotations (e.g., pixel data 1100p identifying a target feature such as a tooth) and tooth contaminant 1102 may be rendered on display screen 1200. The panoramic image view may be have generated as described herein for any of panoramic image view 600, 800, 1100 or otherwise herein.

In some aspects, a recommendation may be generated based on at least one of a panoramic image view, a plurality of images, and/or position data as determined as described herein. For example, the recommendation may provide guidance to the user for use of the scanning device or may comprise a product recommendation As further shown for FIG. 12, an identification 1212, based on feature(s) identifiable within panoramic image view 1100, may be rendered on display screen 1200. The identification may result in a message 1212m comprising an identification corresponding to the panoramic image view (e.g., panoramic image view 1100). Message 1212m includes an identification that plaque was detected in the oral area of the user. In the example of FIG. 12, the identification may be based on the pixel data of panoramic image view 1100.

In some aspects, a recommendation may generated based on the identification 1212. That is, digital image stitching method may further comprising generating a recommendation based on at least one of: the panoramic image view, the plurality of images, and/or the position data. In the example of FIG. 12, recommendation and/or guidance are provided in message 1212m the user for eliminating the tooth contaminate 1102 (e.g., plaque), where "flossing and brushing with a cavity protection tooth paste is recommended."

Still, in further aspects, the digital image stitching method may further comprise recommending a product based on the panoramic image view (e.g., panoramic image view 1100). For example, a product recommendation 12222 may correspond to the identification 1212 as detected within the panoramic image view 1100. In the example of FIG. 12, user interface 1202 renders or provides a recommended product (e.g., manufactured product 1224r, such as cavity prevention toothpaste) as determined by the panoramic imaging app 108 and the related image analysis of panoramic image view 1100 and its pixel data. In the example of FIG. 12, this is indicated and annotated (1224p) on user interface 1202.

User interface 1202 may further include a selectable user interface (UI) button 1224s to allow the user (to select for purchase or shipment the corresponding product (e.g., manufactured product 1224r). In some aspects, selection of selectable UI button 1224s may cause the recommended product(s) to be shipped to the user and/or may notify a third party that the individual is interested in the product(s). For example, either user computing device 111c1 and/or imaging server(s) 102 may initiate, based on the indication 1212 or tooth contaminant, the manufactured product 1224r (e.g., toothpaste) for shipment to the user. In such aspects, the product may be packaged and shipped to the user.

In various aspects, the product recommendation 1222 is rendered on the display screen in real-time or near-real time, during, or after generating the panoramic image view (e.g., panoramic image view 1100). That is, a panoramic image view may be shown in real-time (live) or near-real time, on the GUI as illustrated for FIGS. 1 and 12.

In some aspects, a user may provide a new image. For example, as shown in the example of FIG. 12, the user may select selectable button 1212i for reanalyzing (e.g., either locally at computing device 111c1 or remotely at imaging server(s) 102) a new digital image. Selectable button 1212i may cause user interface 1202 to prompt the user to attach or capture for analyzing new image(s). User computing device 111c1 may receive the new image for generation of a new panoramic image view as described herein. The new image may be compared to previous images to track information of the application area overtime, e.g., such as the evolution of tooth contaminant 1102 over time as described herein.

ASPECTS OF THE DISCLOSURE

The following aspects are provided as examples in accordance with the disclosure herein and are not intended to limit the scope of the disclosure.

1. A digital image stitching method for generating one or more panoramic image views, the digital image stitching method comprising: capturing, by a camera of a scanner device, a plurality of digital images depicting a target feature within an application area, the plurality of digital images comprising at least a first image and a second image; capturing, by a sensor coupled to the scanner device, motion data as the scanner device moves relative to the target feature; determining relative position data based on the motion data, the relative position data comprising at least first position data corresponding to the first image and second position data corresponding to the second image; generating, based on the relative position data, at least one of an angle or a position of the second image relative to the first image; and generating, based on image matching of the second image with the first image based on the angle or the position of the second image, a panoramic image view depicting the target feature in a wider field of view of the application area than either the first image or the second image.

2. The digital image stitching method of aspect 1, wherein generating the angle of the second image comprises: determining a tilt angle for the second image based on an angular velocity change from the first image to the second image; and rotating the second image by the tilt angle.

3. The digital image stitching method of any one of aspects 1-2, wherein generating the position of the second image comprises: determining a first image feature within the first image; determining a second image feature within the second image, the first image feature corresponding to the second image feature; determining a coordinate distance between the first image feature and the second image feature; and setting the position of the second image by offsetting the second image from the first image by the coordinate distance.

4. The digital image stitching method of any one of aspects 1-3 further comprising: automatically detecting the target feature within the application area causing the plurality of images to be captured.

5. The digital image stitching method of any one of aspects 1-4, wherein the plurality of digital images depict one or more of: one or more teeth, soft human tissue, or an artificial oral material.

6. The digital image stitching method of any one of aspects 1-5, wherein the camera comprises one or more of: an intraoral camera, a floor camera, a skin camera, an oral treatment device comprising a camera, a toothbrush comprising a camera, or a mouth piece comprising a camera.

7. The digital image stitching method of any one of aspects 1-6, wherein the sensor comprises one or more of: a gyroscope, an accelerator, a magnetic sensor, or an inertial measurement unit (IMU).

8. The digital image stitching method of any one of aspects 1-7, wherein the application area is one of an oral area, a skin area, or a floor area.

9. The digital image stitching method of any one of aspects 1-8, wherein the panoramic image view is generated following completion of one or more: (a) determining that positioning of the plurality of images in the application area equals or exceeds a maximum coordinate distance; or (b) determining that a threshold number of digital images of the plurality of images has been obtained.

10. The digital image stitching method of claim 9, wherein the application area is an oral area, and wherein the panoramic image view is generated following completion of determining that a minimum number of teeth have been scanned in the oral area.

11. The digital image stitching method of any one of aspects 1-10, wherein the application area is an oral area, and wherein the digital image stitching method further comprises: predicting zonal locations within the oral area based on one or more of: the panoramic image view; or the panoramic image view and the position data.

12. The digital image stitching method of any one of aspects 1-11, wherein the application area is an oral area comprising one or more zonal locations including at least a first zonal location and a second zonal location, and wherein the image matching of the second image with the first image is further based on a positive indication that each of the second image and the first image are within the first zonal location.

13. The digital image stitching method of any one of aspects 12, wherein the plurality of digital images as captured by the camera further comprise a third image, and wherein the digital image stitching method further comprises: determining that the third image depicts the second zonal location; and forgoing image matching of the third image with either of the second image or the first image based on the third image being in located the second zonal location, the second zonal location being different from the first zonal location.

14. The digital image stitching method of any one of aspects 1-13, wherein the application area is an oral area, and wherein the digital image stitching method further comprises: predicting a tooth position of one or more teeth depicted within the oral area based on one or more of: the panoramic image view; or the panoramic image view and the position data.

15. The digital image stitching method of any one of aspects 1-14, wherein the application area is an oral area, and wherein the digital image stitching method further comprises: identifying a user based on one or more unique oral features of the user depicted by the panoramic image view.

16. The digital image stitching method of any one of aspects 1-15, wherein the application area is an oral area, and wherein the digital image stitching method further comprises: identifying a user based on one or more unique scan behaviors of the position data.

17. The digital image stitching method of any one of aspects 1-16, wherein the application area is an oral area, and wherein the digital image stitching method further comprises: identifying an indication of a tooth contaminant on one or more teeth depicted within the panoramic image view.

18. The digital image stitching method of aspect 17 further comprising: generating a second panoramic image view at a second time; identifying a second indication of a tooth contaminant on one or more teeth depicted within the second panoramic image view; and determine a tooth contaminant evolution between the second indication of the tooth contaminant and the indication of the tooth contaminant.

19. The digital image stitching method of any one of aspects 1-18 further comprising rendering the panoramic image view on a graphic user interface (GUI).

20. The digital image stitching method of any one of aspects 1-19 further comprising generating a recommendation based on at least one of: the panoramic image view, the plurality of images, or the position data.

21. The digital image stitching method of any one of aspects 1-20 further comprising outputting a control signal based on at least one of: the panoramic image view, the plurality of images, or the position data, wherein the control signal controls an operation of at least the scanning device, the camera, or the sensor.

22. The digital image stitching method of any one of aspects 1-21 further comprising recommending a product based on the panoramic image view.

23. The digital image stitching method of any one of aspects 1-22, wherein the scanner device is a hand-held device or a clip-on device.

24. The digital image stitching method of any one of aspects 1-23 further comprising: determining one or more zonal locations within the application area; generating, based on the image matching of the second image with the first image based on the angle or the position of the second image, a distance moved in a horizontal direction and in a vertical direction, the distance moved defining a movement of the camera from a first position when the first image was captured to a second position when the second image was captured; generating, based on the distance moved in the horizontal direction and the vertical direction, a total distance defining a total movement; determining, based on the total movement, at least one of (i) a coverage amount occurring within at least one of the one or more zonal locations, or (ii) a trajectory value defining a trajectory within at least one of the one or more zonal locations; and generating an indication of whether a successful scan occurred based on at least one of the coverage amount or the trajectory value.

25. The digital image stitching method of aspect 1, wherein the plurality of images captured by the camera comprise a third image, and wherein the digital image stitching method further comprises: determining that the third image lacks a quality criterion; and discarding the third image from use in generating the panoramic image view.

26. The digital image stitching method of aspect 1, wherein the scanner device comprises a physical distancing element configured to maintain a constant distance between the camera and the target feature or the application area.

27. A digital image stitching system configured to generate one or more panoramic image views, the digital image stitching system comprising: a scanner device comprising a camera configured to capture digital images; a sensor coupled to the scanner device and configured to capture motion data; one or more processors communicatively coupled to the scanner device; and a computer readable medium storing computing instructions configured to execute on the one or more processors, wherein the computing instructions, when executed by the one or more processors, cause the one or more processors to: capture, by the camera, a plurality of digital images depicting a target feature within an application area, the plurality of digital images comprising at least a first image and a second image, capture, by the sensor, the motion data as the scanner device moves relative to the target feature; determine relative position data based on the motion data, the relative position data comprising at least first position data corresponding to the first image and second position data corresponding to the second image, generate, based on the relative position data, at least one of an angle or a position of the second image relative to the first image, and generate, based on image matching of the second image with the first image based on the angle or the position of the second image, a panoramic image view depicting the target feature in a wider field of view of the application area than either the first image or the second image.

28. A tangible, non-transitory computer-readable medium storing instructions for generating one or more panoramic image views, that when executed by one or more processors cause the one or more processors to: capture, by a camera of a scanner device, a plurality of digital images depicting a target feature within an application area, the plurality of digital images comprising at least a first image and a second image; capture, by a sensor coupled to the scanner device, motion data as the scanner device moves relative to the target feature; determine relative position data based on the motion data, the relative position data comprising at least first position data corresponding to the first image and second position data corresponding to the second image; generate, based on the relative position data, at least one of an angle or a position of the second image relative to the first image; and generate, based on image matching of the second image with the first image based on the angle or the position of the second image, a panoramic image view depicting the target feature in a wider field of view of the application area than either the first image or the second image.

29. A digital image stitching method comprising: capturing, by a camera of a scanner device, a plurality of digital images depicting a target feature within an application area, the plurality of digital images comprising at least a first image and a second image; capturing, by a sensor coupled to the scanner device, motion data as the scanner device moves relative to the target feature; determining relative position data based on the motion data, the relative position data comprising at least first position data corresponding to the first image and second position data corresponding to the second image; generating, based on the relative position data, at least one of an angle or a position of the second image relative to the first image; and generating, based on image matching of the first image with the second image and one or more distances moved in respective horizontal and vertical directions, a total distance defining a total movement.

30. The digital image stitching method of aspect 29 further comprising generating a panoramic image view depicting the target feature in a wider field of view of the application area than either the first image or the second image.

31. A digital imaging method for determining a successful scan completion of a scan of a zone, the digital imaging method comprising: capturing, by a camera of a scanner device, a plurality of digital images depicting a target feature within an application area, the plurality of digital images comprising at least a first image and a second image; capturing, by a sensor coupled to the scanner device, motion data as the scanner device moves relative to the target feature; determining relative position data based on the motion data, the relative position data comprising at least first position data corresponding to the first image and second position data corresponding to the second image; generating, based on the relative position data, at least one of an angle or a position of the second image relative to the first image; generating, based on image matching of the second image with the first image based on the angle or the position of the second image, a distance moved in a horizontal direction or a distance moved in a vertical direction, the distance defining movement of the camera when capturing the first image and the second image; and determining a zone scan completion based on the distance moved in the horizontal direction or the distance moved in the vertical direction, the zone scan completion defining a total distance of a total movement of the scan with respect to at least one preset threshold value.

32. The digital imaging method of aspect 31 further comprising: determining the zone scan completion further based on a required amount of the plurality of images collected within the zone with respect to at least one preset threshold number defining the completion of one or more zones.

ADDITIONAL CONSIDERATIONS

Although the disclosure herein sets forth a detailed description of numerous different aspects, it should be understood that the legal scope of the description is defined by the words of the claims set forth at the end of this patent and equivalents. The detailed description is to be construed as exemplary only and does not describe every possible aspect since describing every possible aspect would be impractical. Numerous alternative aspects may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain aspects are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example aspects, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example aspects, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example aspects, the processor or processors may be located in a single location, while in other aspects the processors may be distributed across a number of locations.

The performance of certain of the operations may be distributed among the one or more processors, not only residing within a single machine, but deployed across a number of machines. In some example aspects, the one or more processors or processor-implemented modules may be located in a single geographic location (e.g., within a home environment, an office environment, or a server farm). In other aspects, the one or more processors or processor-implemented modules may be distributed across a number of geographic locations.

This detailed description is to be construed as exemplary only and does not describe every possible aspect, as describing every possible aspect would be impractical, if not impossible. A person of ordinary skill in the art may implement numerous alternate aspects, using either current technology or technology developed after the filing date of this application.

Those of ordinary skill in the art will recognize that a wide variety of modifications, alterations, and combinations can be made with respect to the above described aspects without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A digital image stitching method for generating one or more panoramic image views, the digital image stitching method comprising:
   capturing, by a camera of a scanner device, a plurality of digital images depicting a target feature within an application area, the plurality of digital images comprising at least a first image and a second image;
   capturing, by a sensor coupled to the scanner device, motion data as the scanner device moves relative to the target feature;
   determining relative position data based on the motion data, the relative position data comprising at least first position data corresponding to the first image and second position data corresponding to the second image;
   generating, based on the relative position data, at least one of an angle or a position of the second image relative to the first image; and
   generating, based on image matching of the second image with the first image based on the angle or the position of the second image, a panoramic image view depicting the target feature in a wider field of view of the application area than either the first image or the second image;
   wherein the panoramic image view is generated following completion of one or more: (a) determining that positioning of the plurality of images in the application area equals or exceeds a maximum coordinate distance; (b) determining that a threshold number of digital images of the plurality of images has been obtained;
   wherein the application area is an oral area, and wherein the panoramic image view is generated following completion of determining that a minimum number of teeth have been scanned in the oral area.

2. The digital image stitching method of claim 1, wherein generating the angle of the second image comprises:

determining a tilt angle for the second image based on an angular velocity change from the first image to the second image; and rotating the second image by the tilt angle.

3. The digital image stitching method of claim 1, wherein generating the position of the second image comprises:

determining a first image feature within the first image;

determining a second image feature within the second image, the first image feature corresponding to the second image feature;

determining a coordinate distance between the first image feature and the second image feature; and setting the position of the second image by offsetting the second image from the first image by the coordinate distance.

4. The digital image stitching method of claim 1 further comprising:

automatically detecting the target feature within the application area causing the plurality of images to be captured.

5. The digital image stitching method of claim 1, wherein the plurality of digital images depict one or more of: one or more teeth, soft human tissue, or an artificial oral material.

6. The digital image stitching method of claim 1, wherein the camera comprises one or more of: an intraoral camera, a floor camera, a skin camera, an oral treatment device comprising a camera, a toothbrush comprising a camera, or a mouth piece comprising a camera.

7. The digital image stitching method of claim 1, wherein the sensor comprises one or more of: a gyroscope, an accelerator, a magnetic sensor, or an inertial measurement unit (IMU).

8. The digital image stitching method of claim 1, wherein the application area is one of an oral area, a skin area, or a floor area.

9. The digital image stitching method of claim 1, wherein the application area is an oral area, and wherein the digital image stitching method further comprises:

predicting zonal locations within the oral area based on one or more of: the panoramic image view; or the panoramic image view and the position data.

10. The digital image stitching method of claim 1, wherein the application area is an oral area comprising one or more zonal locations including at least a first zonal location and a second zonal location, and wherein the image matching of the second image with the first image is further based on a positive indication that each of the second image and the first image are within the first zonal location.

11. The digital image stitching method of claim 10, wherein the plurality of digital images as captured by the camera further comprise a third image, and wherein the digital image stitching method further comprises:

determining that the third image depicts the second zonal location; and forgoing image matching of the third image with either of the second image or the first image based on the third image being in located the second zonal location, the second zonal location being different from the first zonal location.

12. The digital image stitching method of claim 1, wherein the application area is an oral area, and wherein the digital image stitching method further comprises:

predicting a tooth position of one or more teeth depicted within the oral area based on one or more of: the panoramic image view; or the panoramic image view and the position data.

13. The digital image stitching method of claim 1, wherein the application area is an oral area, and wherein the digital image stitching method further comprises:

identifying a user based on one or more unique oral features of the user depicted by the panoramic image view.

14. The digital image stitching method of claim 1, wherein the application area is an oral area, and wherein the digital image stitching method further comprises:

identifying a user based on one or more unique scan behaviors of the position data.

15. The digital image stitching method of claim 1, wherein the application area is an oral area, and wherein the digital image stitching method further comprises:

identifying an indication of a tooth contaminant on one or more teeth depicted within the panoramic image view.

16. The digital image stitching method of claim 15 further comprising:

generating a second panoramic image view at a second time;

identifying a second indication of a tooth contaminant on one or more teeth depicted within the second panoramic image view; and determine a tooth contaminant evolution between the second indication of the tooth contaminant and the indication of the tooth contaminant.

17. The digital image stitching method of claim 1 further comprising rendering the panoramic image view on a graphic user interface (GUI).

18. The digital image stitching method of claim 1 further comprising generating a recommendation based on at least one of: the panoramic image view, the plurality of images, or the position data.

19. The digital image stitching method of claim 1 further comprising outputting a control signal based on at least one of: the panoramic image view, the plurality of images, or the position data, wherein the control signal controls an operation of at least the scanning device, the camera, or the sensor.

20. The digital image stitching method of claim 1 further comprising recommending a product based on the panoramic image view.

21. The digital image stitching method of claim 1, wherein the scanner device is a hand-held device or a clip-on device.

22. The digital image stitching method of claim 1 further comprising:

determining one or more zonal locations within the application area;

generating, based on the image matching of the second image with the first image based on the angle or the position of the second image, a distance moved in a horizontal direction and in a vertical direction, the distance moved defining a movement of the camera from a first position when the first image was captured to a second position when the second image was captured;

generating, based on the distance moved in the horizontal direction and the vertical direction, a total distance defining a total movement;

determining, based on the total movement, at least one of (i) a coverage amount occurring within at least one of the one or more zonal locations, or (ii) a trajectory value defining a trajectory within at least one of the one or more zonal locations; and generating an indication of whether a successful scan occurred based on at least the coverage amount or the trajectory value.

23. The digital image stitching method of claim 1, wherein the plurality of images captured by the camera comprise a third image, and wherein the digital image stitching method further comprises:
  determining that the third image lacks a quality criterion; and
  discarding the third image from use in generating the panoramic image view.

24. The digital image stitching method of claim 1, wherein the scanner device comprises a physical distancing element configured to maintain a constant distance between the camera and the target feature or the application area.

25. A digital image stitching system configured to generate one or more panoramic image views, the digital image stitching system comprising:
  a scanner device comprising a camera configured to capture digital images;
  a sensor coupled to the scanner device and configured to capture motion data;
  one or more processors communicatively coupled to the scanner device; and
  a non-transitory computer readable medium storing computing instructions configured to execute on the one or more processors, wherein the computing instructions, when executed by the one or more processors, cause the one or more processors to:
  capture, by the camera, a plurality of digital images depicting a target feature within an application area, the plurality of digital images comprising at least a first image and a second image,
  capture, by the sensor, the motion data as the scanner device moves relative to the target feature;
  determine relative position data based on the motion data, the relative position data comprising at least first position data corresponding to the first image and second position data corresponding to the second image,
  generate, based on the relative position data, at least one of an angle or a position of the second image relative to the first image, and
  generate, based on image matching of the second image with the first image based on the angle or the position of the second image, a panoramic image view depicting the target feature in a wider field of view of the application area than either the first image or the second image;
  wherein the panoramic image view is generated following completion of one or more: (a) determining that positioning of the plurality of images in the application area equals or exceeds a maximum coordinate distance; (b) determining that a threshold number of digital images of the plurality of images has been obtained;
  wherein the application area is an oral area, and wherein the panoramic image view is generated following completion of determining that a minimum number of teeth have been scanned in the oral area.

26. A tangible, non-transitory computer-readable medium storing instructions for generating one or more panoramic image views, that when executed by one or more processors cause the one or more processors to:
  capture, by a camera of a scanner device, a plurality of digital images depicting a target feature within an application area, the plurality of digital images comprising at least a first image and a second image;
  capture, by a sensor coupled to the scanner device, motion data as the scanner device moves relative to the target feature;
  determine relative position data based on the motion data, the relative position data comprising at least first position data corresponding to the first image and second position data corresponding to the second image;
  generate, based on the relative position data, at least one of an angle or a position of the second image relative to the first image; and
  generate, based on image matching of the second image with the first image based on the angle or the position of the second image, a panoramic image view depicting the target feature in a wider field of view of the application area than either the first image or the second image;
  wherein the panoramic image view is generated following completion of one or more: (a) determining that positioning of the plurality of images in the application area equals or exceeds a maximum coordinate distance; (b) determining that a threshold number of digital images of the plurality of images has been obtained;
  wherein the application area is an oral area, and wherein the panoramic image view is generated following completion of determining that a minimum number of teeth have been scanned in the oral area.

27. A digital image stitching method comprising:
  capturing, by a camera of a scanner device, a plurality of digital images depicting a target feature within an application area, the plurality of digital images comprising at least a first image and a second image;
  capturing, by a sensor coupled to the scanner device, motion data as the scanner device moves relative to the target feature;
  determining relative position data based on the motion data, the relative position data comprising at least first position data corresponding to the first image and second position data corresponding to the second image;
  generating, based on the relative position data, at least one of an angle or a position of the second image relative to the first image; and
  generating, based on image matching of the first image with the second image and one or more distances moved in respective horizontal and vertical directions, a total distance defining a total movement;
  generating a panoramic image view depicting the target feature in a wider field of view of the application area than either the first image or the second image;
  wherein the panoramic image view is generated following completion of one or more: (a) determining that positioning of the plurality of images in the application area equals or exceeds a maximum coordinate distance; (b) determining that a threshold number of digital images of the plurality of images has been obtained;
  wherein the application area is an oral area, and wherein the panoramic image view is generated following completion of determining that a minimum number of teeth have been scanned in the oral area.

28. A digital imaging method for determining a successful scan completion of a scan of a zone, the digital imaging method comprising:
  capturing, by a camera of a scanner device, a plurality of digital images depicting a target feature within an application area, the plurality of digital images comprising at least a first image and a second image;
  capturing, by a sensor coupled to the scanner device, motion data as the scanner device moves relative to the target feature;

determining relative position data based on the motion data, the relative position data comprising at least first position data corresponding to the first image and second position data corresponding to the second image;

generating, based on the relative position data, at least one of an angle or a position of the second image relative to the first image;

generating, based on image matching of the second image with the first image based on the angle or the position of the second image, a distance moved in a horizontal direction or a distance moved in a vertical direction, the distance defining movement of the camera when capturing the first image and the second image; and determining a zone scan completion based on the distance moved in the horizontal direction or the distance moved in the vertical direction, the zone scan completion defining a total distance of a total movement of the scan with respect to at least one preset threshold value;

generating a panoramic image view depicting the target feature in a wider field of view of the application area than either the first image or the second image;

wherein the panoramic image view is generated following completion of one or more: (a) determining that positioning of the plurality of images in the application area equals or exceeds a maximum coordinate distance; (b) determining that a threshold number of digital images of the plurality of images has been obtained.

29. The digital imaging method of claim 28 further comprising:

determining the zone scan completion further based on a required amount of the plurality of images collected within the zone with respect to at least one preset threshold number defining the completion of one or more zones.

* * * * *